(12) United States Patent
Pratsevall Garcia et al.

(10) Patent No.: US 10,943,672 B2
(45) Date of Patent: Mar. 9, 2021

(54) WEB-BASED COMPUTER-AIDED METHOD AND SYSTEM FOR PROVIDING PERSONALIZED RECOMMENDATIONS ABOUT DRUG USE, AND A COMPUTER-READABLE MEDIUM

(71) Applicant: AB-Biotics S.A., Barcelona (ES)

(72) Inventors: Jordi Pratsevall Garcia, Girona (ES); David Redondo Amado, Barcelona (ES); Miquel Tuson Segarra, Barcelona (ES); Silvia Vilches Saez, Barcelona (ES); Jordi Espadaler Mazo, Girona (ES); Ariana Salavert Larrosa, Barcelona (ES); Miquel Angel Bonachera Sierra, Girona (ES)

(*) Notice: Subject to any disclaimer, the term of this patent is extended or adjusted under 35 U.S.C. 154(b) by 1168 days.

(21) Appl. No.: 15/104,071

(22) PCT Filed: Dec. 10, 2014

(86) PCT No.: PCT/IB2014/002715
§ 371 (c)(1),
(2) Date: Jun. 13, 2016

(87) PCT Pub. No.: WO2015/087140
PCT Pub. Date: Jun. 18, 2015

(65) Prior Publication Data
US 2016/0314251 A1    Oct. 27, 2016

Related U.S. Application Data

(60) Provisional application No. 61/915,077, filed on Dec. 12, 2013.

(51) Int. Cl.
*G16C 20/30* (2019.01)
*G16H 10/60* (2018.01)
(Continued)

(52) U.S. Cl.
CPC ............ *G16C 20/30* (2019.02); *A61B 5/4839* (2013.01); *G16C 20/10* (2019.02); *G16H 10/60* (2018.01);
(Continued)

(58) Field of Classification Search
CPC .......... G06F 20/20; G06F 40/00; G06F 50/00; G06F 16/16
See application file for complete search history.

(56) References Cited

U.S. PATENT DOCUMENTS

| | | | |
|---|---|---|---|
| 2006/0034508 A1* | 2/2006 | Zhou | G16H 50/70 382/156 |
| 2006/0084071 A1* | 4/2006 | Muchowski | G01N 33/6896 435/6.16 |
| 2014/0304270 A1* | 10/2014 | Torkamani | G16B 40/00 707/740 |

* cited by examiner

*Primary Examiner* — Reginald R Reyes
(74) *Attorney, Agent, or Firm* — Eugenio J. Torres-Oyola; Victor M. Rodriguez-Reyes; Rafael Rodriguez-Muriel

(57) ABSTRACT

The present invention relates to a web-based computer-aided method and a system for providing personalized recommendations about drug use, based on pharmacogenetic information regarding genes and genetic variants associated to metabolism and genes and genetic variants which are not associated to metabolism, and which comprises automatically generating and displaying, by means of a graphical user interface (GUI) of a dynamic webpage, the personalized recommendations highlighting the ones associated to the highest adverse drug reactions.

The present invention also relates to a computer-readable medium which contains program instructions for a computer to perform the method for providing personalized recommendations about drug use of the invention.

The present invention also relates to a web-based computer-aided method and a system for generating a dynamic webpage, and a further computer-readable medium which (Continued)

contains program instructions for a computer to perform the method for generating a dynamic webpage.

14 Claims, 12 Drawing Sheets

(51) Int. Cl.
  *G16C 20/10* (2019.01)
  *G16H 20/10* (2018.01)
  *G16H 70/40* (2018.01)
  *A61B 5/00* (2006.01)
  *H04L 12/24* (2006.01)
  *H04L 29/08* (2006.01)
  *G16B 20/00* (2019.01)
(52) U.S. Cl.
  CPC ............. *G16H 20/10* (2018.01); *G16H 70/40* (2018.01); *H04L 41/22* (2013.01); *H04L 67/02* (2013.01); *G16B 20/00* (2019.02)

WEB-BASED COMPUTER-AIDED METHOD AND SYSTEM FOR PROVIDING PERSONALIZED RECOMMENDATIONS ABOUT DRUG USE, AND A COMPUTER-READABLE MEDIUM

FIELD OF THE INVENTION

The present invention generally relates to a web-based computer-aided method and a system for providing personalized recommendations about drug use, based on pharmacogenetic information regarding genes associated to metabolism and genes which are not associated to metabolism, and which comprises generating and displaying, by means of a graphical user interface (GUI) of a dynamic webpage, the personalized recommendations highlighting the ones associated to the highest adverse drug reactions.

The present invention also relates to a computer-readable medium, which preferably is non-transitory, i.e. tangible, and which contains program instructions for a computer to perform the method for providing personalized recommendations about drug use of the invention.

The present invention also relates to a web-based computer-aided method and a system for generating a dynamic webpage, and a further computer-readable medium which contains program instructions for a computer to perform the method for generating a dynamic webpage.

BACKGROUND OF THE INVENTION

There are different proposals related to computer-aided methods and systems for the generation and providing of personalized recommendations about drug use generally in the form of reports printable and/or displayed in a client display. Some of said proposals are also web-based, i.e. generate and provide said reports via a web service.

Next, some patent documents disclosing such proposals are cited and their relevant background briefly disclosed.

U.S. Pat. No. 8,311,851 B2 discloses a computerized tool and a method for delivery of pharmacogenetic and pharmacological information, interpreting genetic and pharmacologic data by using predictive algorithms, and providing said delivery via graphical user interfaces, in the form of reports, accessible via any network, including the World Wide Web, including Type I reports which include a drug-gene interaction report for selected drugs and Type II reports which include drug-drug interaction reports, where the drugs are selected by the user based on current medications and is generated on the fly in response to patient entries and provided in the form of an interactive webpage with multi-level displays, including for example: ranked warnings on possible drug or herbal interactions specific to the patient's drug regime or proposed prescription use, suggestions for alternative drugs in the same therapeutic class, annotations with links to the medical literature, recommendations for added genetic testing, and so forth.

Different interactions regarding pairs of issues are foreseen in U.S. Pat. No. 8,311,851 B2, including drug-drug, drug-substance, drug-gene, substance-gene, drug-clinical factor, substance-clinical factor, and multiple complex interactions, many of which have been associated with adverse drug interactions, but, although it is broadly stated that a combination of said pair interactions is also possible, no example of such a combination is disclosed at all, not being therefore described in U.S. Pat. No. 8,311,851 B2 any interaction involving three issues are predicted, neither drug-drug-gene, substance-gene-drug, drug-substance-clinical factor nor any other three issues interaction.

The predictions made by the algorithms disclosed by U.S. Pat. No. 8,311,851 B2 can only be done when there is semi-quantitative information about clearance variance for a drug, i.e. pharmacokinetic (PK) data, thus said predictions are clearance predictions, i.e. do not relate to pharmacodynamics (PD), but in most drugs the PK/PD ratio is not linear, and what is really important to know is if a given clearance for a drug involves having to adjust its administering dosage for having a pharmacodynamics effect or not. In other words, with the predictions provided by the method and system of U.S. Pat. No. 8,311,851 B2, it is known what happens when there is a genetic variant and what happens when there is a drug-drug interaction, but not what happens when both, said genetic variant and said drug-drug interaction, occur simultaneously.

U.S. Pat. No. 8,311,851 B2 does not disclose using genetic data which is not related to metabolism.

U.S. Patent Application Pub. No. US 2009/171697 A1 discloses computer-assisted methods and algorithms for targeting a dosing regimen or compound selection to an individual patient, based on population models that incorporate genotype information for genes encoding drug metabolizing enzymes for compounds of interest. Generally, the targeted dosing regimen is provided based on drug concentration profiles. A ranked list of a predictive index of drugs is calculated upon patient specific genetic factors, non-heritable patient factors and drug specific factors, and displayed in a display unit.

Different pharmacokinetic and pharmacodynamics interactions are evaluated, such as drug-drug or drug-disease interactions, but only in pairs, i.e. no interaction of three different elements or issues is disclosed in US 2009/171697 A1.

US 2009/171697 A1 neither disclose any web-based method or system, nor generating personal recommendations according to a risk criterion.

U.S. Pat. No. 8,311,851 discloses a computerized tool and method for delivery of pharmacogenetic and pharmacological information, comprising a core system having algorithms and databases for storing, collating, accessing, cross-referencing, and interpreting genetic and pharmacologic data, with a graphical user interface for a client network of providers of laboratory genetic testing services to access the core services under contract. The pharmacogenetics and pharmacological information used in this US patent are associated only to metabolism, this information does not include information regarding genes and genetic variants which are not associated to metabolism.

US 2011/0082867 discloses a method, system, and computer program product, in which the method includes receiving a patient profile, the patient profile including a patient substance profile identifying a plurality of substances consumed by a patient and at least one patient-specific gene variant. The method also includes identifying a gene associated with a first one of the plurality of substances, and performing a weighing process to determine an interaction between the first substance and the gene. The method also includes producing a summary by the data processing system according to the determined interaction. All the interactions described in this US patent application are associated only to metabolism (mainly with dose adjustment).

Some companies market products for a personalized health medicine, by means of personalized recommendations about drug use built from genetic data of a patient and provided by means of a document which can be displayed in a user display.

One of such companies is Assurex Health, whose product GeneSight® is a computer tool that measures and analyzes important genomic variants affecting the metabolism and response to behavioral health medications in individual patients, and provides with objective genetic-based patient information in advance of making a medication decision for a patient, by means of a written report including personalized recommendations which are color coded following a risk criterion.

Although that written report can be displayed in a user display, GeneSight® does not provide such a report by means of a GUI provided by a webpage, neither static nor dynamic, as none web-based method is implemented by said product of Assurex Health.

The present inventors do not know any proposal which provides a web-based method and system for providing personalized recommendations about drug use, from genetic data regarding both, genes associated to metabolism and genes which are not associated to metabolism, by means of a GUI provided by a dynamic web page.

DESCRIPTION OF THE INVENTION

It is an object of the present invention to offer an alternative to the prior state of the art, with the purpose of providing a method and system for providing personalized recommendations about drug use more elaborated than the ones disclosed by the prior state of the art, including pharmacokinetics and pharmacodynamics, the processing of a high amount of genetic information (so high that it would be unfeasible to be processed by a human and, if so, it could lead to errors in the provided recommendations which could have serious consequences for the patient's health) for generating high quality personalized recommendations and an ease of use of the method and system for a user requesting the personalized recommendations.

The present invention, as will be described below for different aspects, really improves the functioning of the computers used in the prior art proposals, specially adapting them for providing highlighted personalized recommendations in a dynamic manner, through a dynamic web page, by making them apt to allow an adequate distribution of the workload, both at a hardware level, including the network linking the different hardware elements, and also at a software level, by providing them with specially adapted program instructions which themselves constitute structural limitations. The so modified computers allow to dynamically update/recalculate in real time, or almost in real time, the recommendations, according to different input data introduced by the physician and/or by the patient, including data related to pharmacodynamics.

A clear improvement in the technological field related to the automatic generation of personalized recommendations about drug use is also achieved with the present invention, allowing to perform such an automatic generation of personalized recommendation, and the highlighting of some of them, processing a higher quantity and diversity of information than the prior art proposals, including pharmacodynamics information, in such a manner that results are obtained in real time, or almost real time, where said results clearly improve the results obtained with the prior art proposals, thus disposing, or almost disposing, of the human intervention to correct a possibly incorrect or not very accurate result, i.e. a bad recommendation.

Improvements in the generation of a dynamic webpage are also provided by the present invention.

To that end, the present invention relates, in a first aspect, to a web-based computer-aided method for providing personalized recommendations about drug use, comprising performing the following steps:

acquiring genetic information about a patient, including single nucleotide polymorphisms (SNPs), wherein said genetic information includes information regarding genes and genetic variants associated to metabolism and information regarding genes and genetic variants which are not associated to metabolism (such as genes and genetic variants associated to drug response and adverse drug reactions);

processing said acquired genetic information together with selected pharmacogenetic information about several drugs to generate (automatically) personalized pharmacogenetic information for said patient;

automatically generating and displaying on a user display a plurality of personalized recommendations for said patient, regarding several drugs, from said generated personalized pharmacogenetic information; and visually highlighting, among said plurality of displayed personalized recommendations, those recommendations associated to risk of adverse drug reactions, following a risk criterion;

wherein the method comprises generating a dynamic webpage from contents regarding at least said plurality of personalized recommendations, providing a graphical user interface (GUI) from said dynamic webpage, and performing said displaying and visually highlighting of personalized recommendations by means of said graphical user interface (GUI); and wherein at least part of said personalized recommendations do not refer to drug dosage, but to drug response and/or adverse drug reactions, i.e. relate to pharmacodynamics.

For an embodiment, said steps of acquiring and processing are performed by means of one or more processing means having at least one processor and one memory, said dynamic webpage and GUI are, respectively, generated and provided by a web server connected to said processing means or comprising at least part of the processing means or being comprised by the processing means, and said user display is part of or connected to a user computing unit connected to the web server to receive said GUI, implementing a specially adapted client/server architecture where said user computing unit is a thin client or a thick client of said web server and/or of said processing means.

The processing means, the web server and the user computing unit have, each, one or more algorithms, in the form of memory-loaded program instructions executable by the processor included therein, which are specially adapted to automatically perform the above described functions.

For a preferred embodiment, said selected pharmacogenetic information includes descriptive information pieces correlating each drug of said several drugs with the presence/absence of a specific genetic variant, each of said descriptive information pieces having associated thereto a risk degree, the method comprising:

when there is only one of said descriptive information pieces correlating a drug with a respective genetic variant of said genetic information, retrieving said only one descriptive information piece and generating therefrom a personalized recommendation for said patient, regarding said drug, and when there are at least two of said descriptive information pieces correlating a drug with at least two respective genetic variants of said genetic information, retrieving said at least two descriptive information pieces and generating a personalized recommendation for said patient, regarding said drug, by selecting, out of said at least two retrieved description information pieces, the descriptive information piece with the highest risk degree.

Said descriptive information pieces are given, for example, in the form of phrases describing how the presence/absence of a specific genetic variant affects the drug response, drug metabolism and/or adverse drug reactions. A detailed embodiment including several of such phrases will be provided below in a subsequent section of the present specification.

Preferably said drugs are neuropsychiatric drugs, including antipsychotics, antidepressants, mood stabilizers, stimulants, anxiolytics, sedatives and hypnotics, anti-addictives and also including antiparkinsonian drugs, anti-dementia drugs, or drugs for treating epilepsy including anticonvulsants. The term "neuropsychiatric drug" is understood as a drug targeting or acting on the central nervous system, CNS.

Drug response is dependent on both genetic factors and concomitant treatment administration. The importance of this fact is that the consumption of other drugs may enhance the response to a given phenotype. For example, if the patient is poor metabolizer for a given drug because he is a carrier of a SNP which makes him having a low activity in the enzyme that metabolizes said drug, the effect can be enhanced further if he consumes a concomitant medication, being another neuropsychiatric drug or a non neuropsychiatric drug (statins, etc.) that is inhibitor of that enzyme. The psychiatrist usually knows psychiatric drug interactions but not those used for other diseases, therefore integrating all the information in a manual manner is a problem for the doctor that can lead to errors in treatment.

Due to the varying nature of patient response to different types and even dosages of the same antidepressant, doctors currently prescribe antidepressants on a trial and error basis.

In order to solve that problem, the method of the present invention further comprises, for a preferred embodiment, acquiring information about one or more concomitant medications or substances being taken by said patient, and modifying at least part of the personalized recommendations and the way they are displayed, based on the influence of said concomitant medication or substance on the drug response, on the drug levels comprising absorption, distribution, metabolism, and excretion, and/or adverse drug reactions or based on the influence of said drug on the concomitant medication/substance response, on the medication/substance metabolism, and/or adverse medication/substance reactions.

According to an embodiment, the method comprises determining said concomitant medication or substance influence by analyzing the interaction between the three of: said drugs, said one or more concomitant medications or substances and said genetic information, said analysis being carried out, for example, by checking how the concomitant medication or substance alters the metabolizer capacity of the patient with respect to one or more of said drugs.

Said interaction analysis is performed, as per an embodiment, after said generation of personalized pharmacogenetic recommendations, wherein said modifying of at least part of said personalized recommendations is performed on the already generated personalized recommendations.

For an alternative embodiment, the method of the invention comprises performing said interaction analysis as part of the processing of acquired genetic information and selected pharmacogenetic information, said processing thus including the processing of said acquired information about at least one concomitant medication or substance together with said acquired genetic information and said selected pharmacogenetic information, wherein the modifying of at least part of the personalized recommendations takes place during, and forms part of, the generation of personalized recommendations.

For a case where there are at least two concomitant medications or substances, the method comprises, based on the influence of each concomitant medication/substance on said drug or vice versa, generating two or more provisional modified personalized recommendations, each having associated thereto a risk degree, and generating and displaying a final modified personalized recommendation for said patient, regarding said drug, by selecting, out of said two or more provisional modified personalized recommendations, the provisional personalized recommendation with the highest risk degree.

The method of the present invention further comprises, for an embodiment, acquiring information about further personal information of the patient associated to pathologies and/or to habits affecting health (such as smoking or alcohol intake) and/or to physical characteristics including at least one of anthropometric data, ethnicity, age and gender, and modifying at least part of the personalized recommendations and the way they are displayed, including said visually highlighting, based on the influence of said further personal information on the drug response and/or adverse drug reactions.

The embodiment of the just above paragraph can be implemented alternatively or preferably combined with the embodiment regarding the acquiring and use of concomitant medication or substances described above, the latter (i.e. the combined case) for providing a modifying of the personalized recommendations based on the influence of both: the concomitant medication/substance and the further personal information.

Regarding how the personalized recommendations are displayed according to the method of the invention, they can be displayed by any means which allows their clear differentiation and meaning, such as by using different graphical icons or representations, but for a preferred embodiment they are displayed according to a color code, the above described visual highlighting including at least the use of a conspicuous or eye-catching or flashing color (such as red) for the personalized recommendation to be highlighted according to the risk criterion.

For a specific implementation of the method of the invention, said color code is used for displaying:

in red, a personalized recommendation having associated thereto an increased risk of adverse drug reactions;

in amber, a personalized recommendation having associated thereto a lower probability of drug response and/or the need for a specific dosage monitoring;

in green, a personalized recommendation having associated thereto a higher probability of drug response and/or a lower risk of adverse drug reactions; and in white, a personalized recommendation having associated thereto a standard drug response, standard metabolism and/or standard risk of adverse drug reactions.

With respect to the modifying of the way a personalized recommendation is displayed, the method comprises, for some embodiments, changing the color and/or shape of a graphical representation displaying said personalized recommendation on a screen area of said user display, and/or displaying, directly or upon the user clicking a virtual link shown in the user display, additional recommendation information (such as by means of a balloon and/or a pop up window) and/or displaying a symbol overlying or near said screen area, wherein said symbol is selected out of a plurality of different symbols associated to respective different influences, regarding the concomitant medication or substance or said further personal information, on the drug response, on drug levels, and/or on adverse drug reactions.

Said plurality of symbols include symbols associated to at least the next influences, with respect to the drug: there are interactions, there are contraindications, there is relevant information, drug dosage increasing and drug dosage reducing.

For an embodiment, the method of the invention comprises displaying a plurality of charts, each including a plurality of identifiers of respective drugs (such as the name thereof) having the same or a similar purpose, wherein each drug identifier is shown associated to one of said displayed personalized recommendations.

For a particular implementation of said embodiment, the method comprises displaying on the user display, alternately or simultaneously:
 a first screen or first graphical area including a plurality of charts, each including a plurality of identifiers of respective drugs having the same or a similar purpose, wherein each drug identifier is shown associated to one of the user displayed personalized recommendations;
 a second screen or second graphical area including a plurality of fillable boxes to be filled by a user to input information regarding the patient, including concomitant medication or substances and personal information associated to pathologies and/or habits affecting health and/or to physical characteristics, including at least one of anthropometric data, ethnicity, age and gender; and
 a third screen or third graphical area including said plurality of charts having modified at least part of said personalized recommendations and the way they are displayed, based on the influence of concomitant medication or substances and/or of said further personal information on the drug response and/or on adverse drug reactions.

The method of the invention comprises providing an online and interactive service to said user, by means of a web service or platform, said online service including at least said displaying of said plurality of charts on the user display, said filling of said fillable boxes, said modification of the personalized recommendations and display thereof, based on the filled information, and the providing of virtual links shown in the user display to be clicked by the user, via computing input means, to access additional recommendation information to be shown on the user display and/or to be downloaded by the user.

With the aim of improving the generated personalized recommendations, the method of the invention comprises, for an embodiment, performing said generation of the personalized recommendation also based on the outcomes of a learning feedback process performed by the method from statistical information regarding several drugs responses and/or several patients and/or interactions between drugs and concomitant medication or substances and/or interactions between drugs and patients personal information associated to pathologies and/or habits affecting health, and/or to physical characteristics including at least one of anthropometric data, ethnicity, age and gender.

The present invention also relates, in a second aspect, to a web-based system for providing personalized recommendations about drug use, comprising:

means for acquiring genetic information about a patient, including single nucleotide polymorphisms (SNPs), wherein said genetic information includes information regarding genes and genetic variants associated to metabolism and information regarding genes and genetic variants which are not associated to metabolism;
 processing means for processing said acquired genetic information together with selected pharmacogenetic information about several drugs to generate personalized pharmacogenetic information for said patient, and for generating a plurality of personalized recommendations for said patient, regarding several drugs, from said generated personalized pharmacogenetic information;
 user computing means associated to user displaying means arranged and adapted for displaying on the user displaying means said generated personalized recommendations and for visually highlighting, among said plurality of displayed personalized recommendations, those recommendations associated to adverse effects, following a risk criterion;
 a web server having access to contents regarding at least said plurality of personalized recommendations and adapted for generating a dynamic webpage from said contents, for providing a graphical user interface (GUI) from said dynamic webpage, said web server being connected to said user computing means for providing said graphical user interface to the user computing means, wherein said user computing means and associated displaying means are adapted for performing said displaying and visually highlighting of personalized recommendations by means of said graphical user interface (GUI); and
 wherein at least part of said personalized recommendations do not refer to drug dosage, but to drug response and/or adverse drug reactions.

For an embodiment, said means for acquiring genetic information and said processing means have at least one processor and one memory with memory-loaded program instructions executable by said at least one processor to perform said acquiring of genetic information and the processing thereof, said web server is connected to said processing means or comprises at least part of the processing means or is comprised by the processing means, and said user computing means have at least one processor and one memory with memory-loaded program instructions executable by said at least one processor to perform said displaying and visually highlighting of displayed personalized recommendations using said GUI.

The means for acquiring and the processing means can be implemented by one and the same computing entity or by two or more separated computing entities connected to each other.

The processing means, the web server and the user computing unit have one or more algorithms, in the form of memory-loaded program instructions executable by the processors included therein, which are specially adapted to automatically perform the above described functions.

The user computing means are implemented by a user computer which can be any device specially adapted to perform the functions described above, with computing and communication capabilities and having or being connected to at least one display, including, but not limited to, a personal computer, a laptop, a smart phone, a PDA, a tablet, an intelligent watch, or any other handheld computer device, a set top box, a smart TV, programmable consumer electronics, one or more network PCs, a minicomputer system, a mainframe computer system, a robot, a cloud computer, etc.

Regarding the acquiring means, the processing means and the web server, they can be implemented by one or more computing units of any type with computing and communication capabilities and appropriate computer resources (memories, buses, etc.), and associated technical elements (gateways, communication links, interfaces, peripherals, etc.), specially adapted to perform the above described functions according to any workload distribution.

Particularly, the web server can be of any type of known web server, specially adapted for the present invention, such as an Apache HTTP server (preferred option), an IIS web hosting server, a Sun Java system web server or a Jigsaw server, or variations thereof.

Any kind of client-server architecture (2-tier or 3-tier) and computer environment (including local computing and/or remote computing and/or cloud computing) can be implemented between the user computing unit and the web server, and also any appropriate communication network linking the different computing entities of the system can be implemented, including wireless and/or wired links.

According to an embodiment, the system of the present invention comprises a database which stores said selected pharmacogenetic information correlating said several drugs and genetic information, and a plurality of prebuilt recommendations associated thereto, wherein said processing means have access to said database to generate said personalized recommendations by at least looking up the acquired genetic information in said stored selected pharmacogenetic information and extracting therefrom at least the prebuilt recommendations associated thereto.

For an alternative o complementary embodiment, the system of the invention comprises a database which stores said selected pharmacogenetic information, the latter including descriptive information pieces correlating each drug of said several drugs with the presence/absence of a specific genetic variant, each of said descriptive information pieces having associated thereto a risk degree, wherein said processing means have access to said database to generate said personalized recommendations by:
  when there is only one of said descriptive information pieces correlating a drug with a respective genetic variant of said genetic information, retrieving from said database said only one descriptive information piece and generating therefrom a personalized recommendation for said patient, regarding said drug, or
  when there are at least two of said descriptive information pieces correlating a drug with at least two respective genetic variants of said genetic information, retrieving from said database said at least two descriptive information pieces, and generating a personalized recommendation for said patient, regarding said drug, by selecting, out of said at least two retrieved description information pieces, the descriptive information piece with the highest risk degree.

The present invention also relates, in a third aspect, to a computer-readable medium containing program instructions for a computer to perform a web-based method for providing personalized recommendations about drug use, comprising performing the following steps:
  acquiring genetic information about a patient, including single nucleotide polymorphisms (SNPs), wherein said genetic information includes information regarding genes and genetic variants associated to metabolism and information regarding genes and genetic variants which are not associated to metabolism;
  processing said acquired genetic information together with selected pharmacogenetic information about several drugs to generate personalized pharmacogenetic information for said patient;
  generating and displaying a plurality of personalized recommendations for said patient, regarding several drugs, from said generated personalized pharmacogenetic information; and
  visually highlighting, among said plurality of displayed personalized recommendations, those recommendations associated to adverse effects, following a risk criterion;
  wherein the method comprises generating a dynamic webpage from contents regarding at least said plurality of personalized recommendations, providing a graphical user interface (GUI) from said dynamic webpage, and performing said displaying and visually highlighting of personalized recommendations by means of said graphical user interface (GUI); and
  wherein at least part of said personalized recommendations do not refer to drug dosage, but to drug response and/or adverse drug reactions.

The computer-readable medium also contains, for some embodiments, program instructions for a computer to perform the actions of all the above described embodiments of the method of the invention.

For an embodiment, the computer-readable medium is a non-transitory computer-readable medium.

For another embodiment, the computer-readable medium is a transitory computer-readable medium, such as a signal, a carrier wave, etc.

Depending on the embodiment, said computer-readable medium is implemented by one or more computer-readable mediums distributed among different computing units in charge of performing the above described functions, such as the computing entities described above with reference to the system of the present invention (acquiring means, processing means, user computing unit and web server).

A fourth aspect of the invention relates to a web-based computer-aided method for generating a dynamic webpage, comprising performing the following steps:
  acquiring, by means of acquiring means having at least one processor and one memory, genetic information about a patient, including single nucleotide polymorphisms (SNPs), wherein said genetic information includes information regarding genes and genetic variants associated to metabolism and information regarding genes and genetic variants which are not associated to metabolism;
  processing, with said processing means, said acquired genetic information together with selected pharmacogenetic information about several drugs to automatically generate personalized pharmacogenetic information for said patient, and for automatically generating a plurality of personalized recommendations for said patient, regarding several drugs, from said generated personalized pharmacogenetic information;
  performing, by means of a web server connected to said processing means or comprising at least part of the processing means or being comprised by the processing means, the following steps:
    generating a dynamic webpage from contents regarding at least said plurality of personalized recommendations, and
    providing, to a user computing unit connected to the processing means, a graphical user interface (GUI) from said dynamic webpage,
  displaying said generated personalized recommendations on a user display of said user computing unit and visually highlighting on said user display, among said plurality of displayed personalized recommendations, those recommendations associated to risk of adverse drug reactions, following a risk criterion, wherein said displaying and visually highlighting of personalized recommendations is performed by means of said graphical user interface (GUI);

wherein at least part of said personalized recommendations do not refer to drug dosage, but to drug response and/or adverse drug reactions.

The embodiments described with respect to the method of the first aspect of the invention are also valid for the method of the fourth aspect of the invention.

A fifth aspect of the present invention relates to a web-based system for generating a dynamic webpage, comprising:

acquiring means having at least one processor and one memory and adapted for acquiring genetic information about a patient, including single nucleotide polymorphisms (SNPs), wherein said genetic information includes information regarding genes and genetic variants associated to metabolism and information regarding genes and genetic variants which are not associated to metabolism;

processing means having at least one processor and one memory and adapted to process said acquired genetic information together with selected pharmacogenetic information about several drugs, by means of memory-loaded program instructions executable by said at least one processor, to generate personalized pharmacogenetic information for said patient, and for generating a plurality of personalized recommendations for said patient, regarding several drugs, from said generated personalized pharmacogenetic information;

a user computing unit connected to a user display;

a web server connected to said processing means or comprising at least part of the processing means or being comprised by the processing means and also connected to said user computing unit, having access to contents regarding at least said plurality of personalized recommendations and adapted for:

generating a dynamic webpage from said contents, and
providing a graphical user interface (GUI) from said dynamic webpage to said user computing unit;

wherein said user computing unit and said user display are arranged and adapted for displaying on the user display said generated personalized recommendations and for visually highlighting on the user display, among said plurality of displayed personalized recommendations, those recommendations associated to risk of adverse drug reactions, following a risk criterion, performing said displaying and visually highlighting of personalized recommendations by means of said graphical user interface (GUI);

wherein at least part of said personalized recommendations do not refer to drug dosage, but to drug response and/or adverse drug reactions.

The embodiments described with respect to the system of the second aspect of the invention are also valid for the system of the fifth aspect of the invention.

The present invention also relates, in a sixth aspect, to a computer-readable medium containing program instructions for a computer to perform a web-based method for generating a dynamic webpage, comprising performing the following steps:

acquiring genetic information about a patient, including single nucleotide polymorphisms (SNPs), wherein said genetic information includes information regarding genes and genetic variants associated to metabolism and information regarding genes and genetic variants which are not associated to metabolism;

processing said acquired genetic information together with selected pharmacogenetic information about several drugs to generate personalized pharmacogenetic information for said patient and to generate a plurality of personalized recommendations for said patient, regarding several drugs, from said generated personalized pharmacogenetic information;

generating a dynamic webpage from contents regarding at least said plurality of personalized recommendations, providing a graphical user interface (GUI) from said dynamic webpage, displaying said plurality of personalized recommendations for said patient and visually highlighting, among said plurality of displayed personalized recommendations, those recommendations associated to adverse effects, following a risk criterion, wherein said displaying and visually highlighting of personalized recommendations is performed by means of said graphical user interface (GUI);

wherein at least part of said personalized recommendations do not refer to drug dosage, but to drug response and/or adverse drug reactions.

The embodiments described with respect to the computer-readable medium of the third aspect of the invention are also valid for the computer-readable medium of the sixth aspect of the invention.

BRIEF DESCRIPTION OF THE DRAWINGS

The previous and other advantages and features will be better understood from the following detailed description of embodiments, with reference to the attached drawings, which must be considered in an illustrative and non-limiting manner, in which:

FIG. 2 shows a screen shot of a first screen of the dynamic webpage GUI generated and provided by the method of the present invention, for a first embodiment called Example 1, including personalized recommendations about neuropsychiatric drugs use, said first screen being displayed when clicking on the shown "Genetic results" tab and/or as a default screen;

FIG. 5 shows a screen shot of a second screen of the dynamic webpage GUI of the method of the present invention, for a second embodiment called Example 2, said second screen including a plurality of fillable boxes to be filled by a user to input information regarding the patient regarding current treatment, including concomitant medication (Terbinafine has been selected in this case) and psychiatric drug (Amitryptiline has been selected in this case), and environmental factors (none of them have been selected in this case), said second screen being displayed when clicking on the shown "Patient Information" tab;

FIG. 9 shows, as in FIG. 5, a screen shot of the second screen of the dynamic webpage GUI of the method of the present invention, but for a third embodiment, called Example 3, for which, contrary to Example 2, none concomitant medication and psychiatric drug have been selected, and an environmental factor has been selected, particularly in the fillable box called "Kidney disease" the "Severe renal insufficiency" factor has been selected;

DETAILED DESCRIPTION OF SEVERAL EMBODIMENTS

Figure 1:
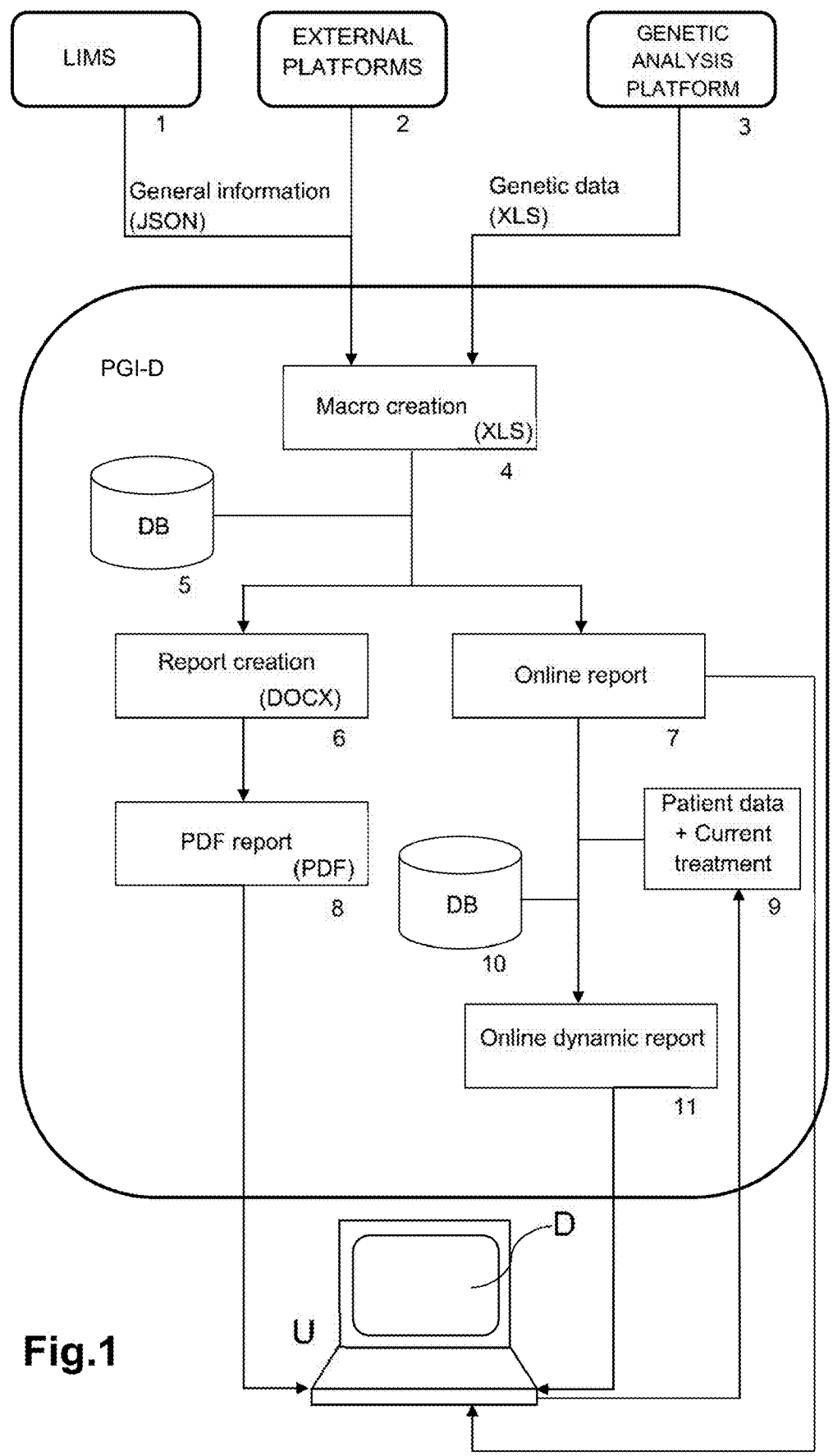
FIG. 1 is a flow chart which depicts the different steps of the method and the different elements of the system of the present invention, for an embodiment.

FIG. 1 shows, for an embodiment, the web-based system for providing personalized recommendations about drug use of the present invention, by means of functional blocks related to the actions performed when implementing the method of the invention.

The system of FIG. 1 comprises means for acquiring genetic information about a patient, including single nucleotide polymorphisms (SNPs), wherein said genetic information includes information regarding genes and genetic variants associated to metabolism and information regarding genes and genetic variants which are not associated to metabolism, wherein said means are illustrated as three blocks 1, 2, 3, where block 3 is a genetic analysis platform that generates genetic data in the form of an XLS file, from a patient genetic sample, and blocks 1 and 2 are, respectively, the managing program LIMS (Laboratory Information Management System), implemented in a respective platform, and external platforms which generate general data (such as sample number, sample type, etc.) in the form of information packets (JSON). Each of said platforms 1, 2, 3 includes one or more computing units, with their respective processors, memories, buses, etc.

Following with the description of FIG. 1, inside the entity referred as PGI-D, at box 4 processing means of the system of the invention creates a macro in the form of a XLS file, containing both the genetic results and the general data about the genetic sample received from blocks 1, 2 and 3.

By processing the information included in said generated macro together with information stored in database 5, including pharmacogenetic information related to several drugs and, for example, phrases correlating each drug with the presence/absence of a specific genetic variant, recommendations, etc., the processing means generate, at one hand, at box 6, a results report in the form of a text document, such as a Microsoft Word© DOCX document containing all the retrieved information in an easily understandable form, and, at the other hand, at box 7, a results report which can be consulted online and which will be the base on which to work for obtaining the final result.

The text report created at 6 is stored as a PDF file at 8 and kept stored in memory means of the PGI-D such that users can download it therefrom to their user computing devices, via web.

The online results report created at 7 includes a plurality of personalized recommendations for the patient, regarding several drugs, with some of them to be visually highlighted if associated to adverse effects, following a risk criterion, when displayed by means of a GUI provided by a dynamic webpage generated by means of a web server of the system of the invention, said web server (which must be understood as been depicted in FIG. 1 as including part or all of the illustrated PGI-D entity) being connected to user computing means for providing said GUI thereto in order the user computing means and associated displaying means perform the displaying and visually highlighting of personalized recommendations by means of said GUI, by accessing to a web address.

The user can just consult said report 7 displayed on the displaying means of his computing means (in a first screen, such as the one shown in FIG. 2) or he can input (in a second screen, such as the one shown in FIG. 5), as indicated at block 9, further patient information together with concomitant medication he is currently taking.

Figure 6:
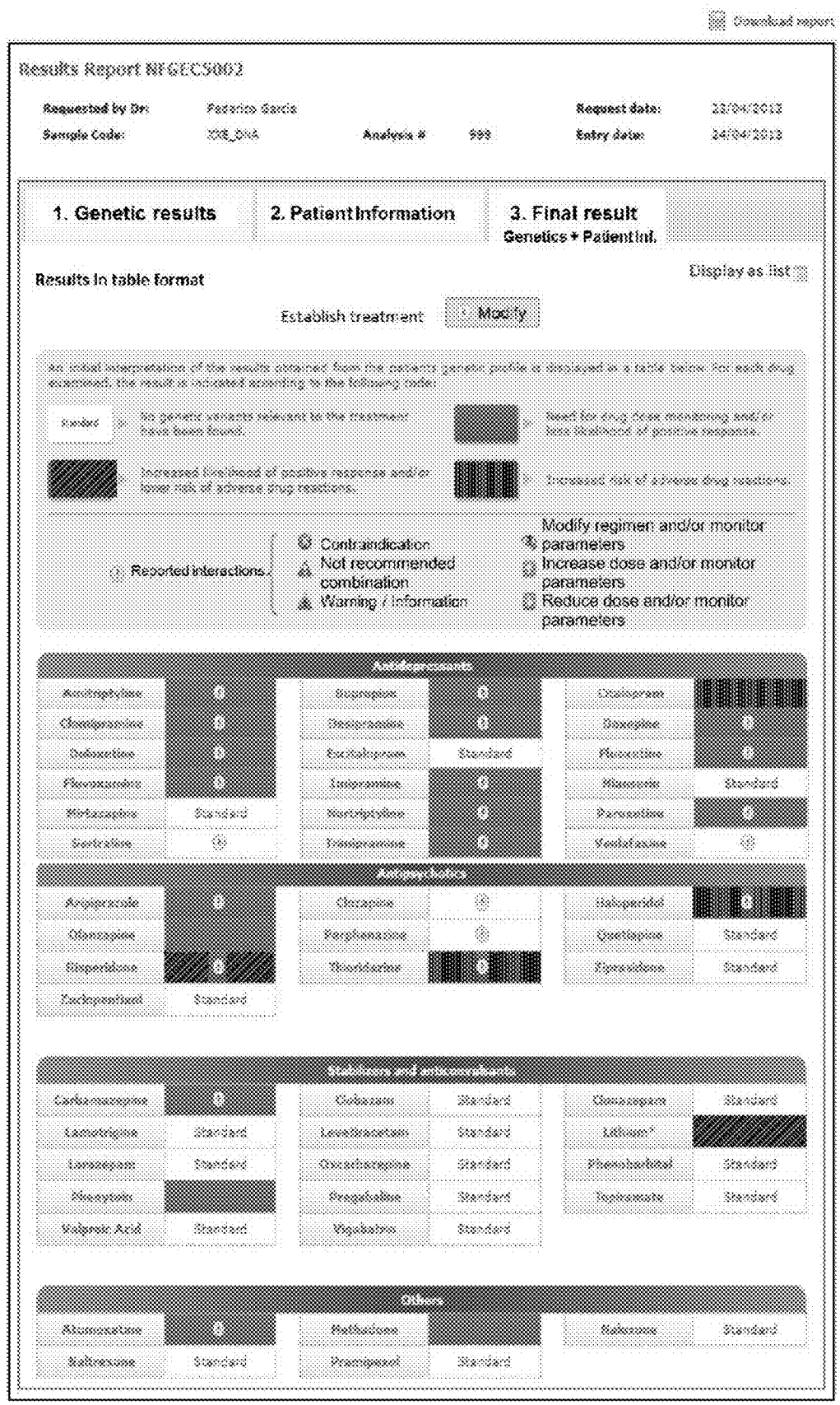
FIG. 6 shows, also for Example 2, a screen shot of a third screen of the dynamic webpage GUI of the method of the present invention, which corresponds to the first screen shown in FIG. 2 but once the displayed recommendation information has been modified as a response to the information inputted by the user in the second screen according to FIG. 5.

The PGI-D, by combining information included in the online report of 7 and the information inputted at 9 and data stored at database 10 (for example phrases regarding interactions between drug and concomitant medication or environmental factor), generates a new online version of the results report at block 11 (in a third screen, such as the one shown in FIG. 6).

Figure 13:
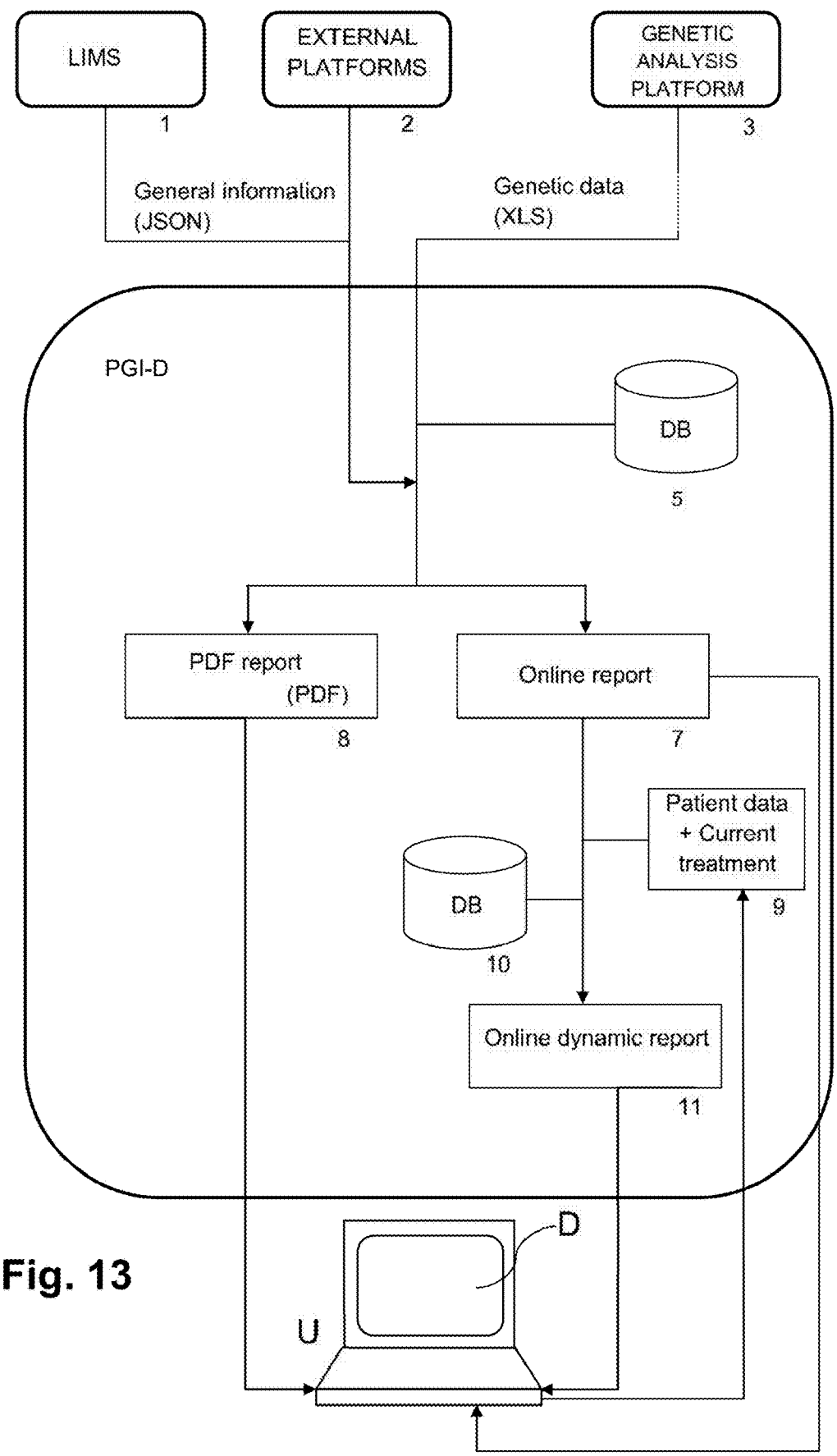
FIG. 13 is a flow chart alternative to that of FIG. 1, and which depicts the different steps of the method and the different elements of the system of the present invention, for another embodiment.

FIG. 13 shows an alternative embodiment to the one of FIG. 1, doing without some of the functional blocks illustrated in FIG. 1, particularly blocks 4 and 6.

The operation of the web-system for the embodiment of FIG. 13 is similar to that of FIG. 1, but dispensing with the functions performed, for the embodiment of FIG. 1, by blocks 4 and 6.

Hence, the operation of the system of the invention, according to the embodiment of FIG. 13, is as follows:

To generate the report in PDF the system, particularly the means for acquiring genetic information, captures, on one hand, genetic data from an excel file (XLS) generated by the genetic analysis platform 3 and, on the other hand, general data (such as sample number, type, etc.) from packets (JSON) generated by external platforms 2 (such as GSK) and program management LIMS 1.

From this data and data stored in the database 5 of the PGI-D (e.g. phrases, recommendations, etc.) the system generates, on one hand, the results report, at block 8, which is a PDF file that contains all the information in an understandable manner and that is stored in memory so that users can download, and also, at block 7, another report of results (online report) which will be available online and that will be the basis on which to work for obtaining the final result.

When the online report is already generated, the user can access the web, through his user computer U, and view the online report. He will also have the option to enter patient information together with information about treatments that are currently taking, at block 9. The PGI-D, based on the primary results report, i.e. on the online report generated at 7, on the information entered by the user at 9 and on data available in database 10 (such as sentences about interactions) generates a new version of the online results report, at block 11, combining all that information.

The PGI-D is the main entity of the system of the invention and includes the databases 5 and 10 and the above mentioned processing means, which in FIGS. 1 and 13 are illustrated only schematically by means of the functional tasks they perform, i.e. by blocks 4 and 6 for FIG. 1, and blocks 7, 8, 9 and 11 for FIGS. 1 and 13, as they can be, at a hardware level, be implemented in many different ways, including local HW portions (including the user computing device U) and/or remote HW portions (including at least the web server S), for performing said functional tasks by means of local and/or remote processing and/or in centralized or distributed environments (such as a distributed cloud computing environment) by means of specially adapted memory-loaded program instructions.

Figure 12:
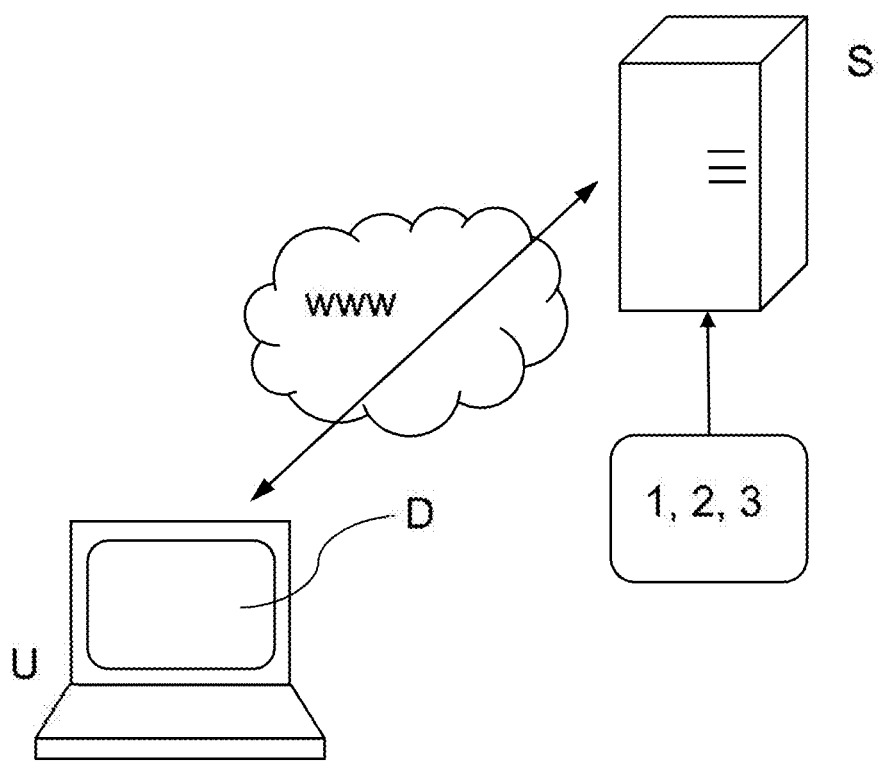
FIG. 12 schematically shows the system of the present invention for an embodiment.

In FIG. 12 a schematic representation of the system of the present invention is depicted, where the user computing means and corresponding display means are illustrated as a computer U and respective computer screen D, the web server is indicated by reference S, the Internet network through which they are bidirectionally connected is indicated as WWW and the platforms 1, 2, 3 described above with reference to FIGS. 1 and 13 are shown in FIG. 12 by means of only one block 1, 2, 3.

For this simple embodiment of FIG. 12, the blocks included in the PGI-D entity of FIGS. 1 and 13 are included in web server S, while the user computer U is bidirectionally connected to said server S via internet to receive the online reports generated at 7 and 11, displaying them in the form of a GUI in computer screen D, and to download the PDF report of 8, if requested by the user, and also to access the web server S to input the patient information at 9 via an interactive screen of said GUI.

In FIGS. 1 and 13, user computer U and respective computer screen D have also been depicted, together with respective arrow lines departing from blocks 7, 8, 11 and going towards user computer U to provide the latter with the above mentioned reports, and also together with a further arrow line which departs from user computer U an goes towards block 9 to graphically show the above described input of patient information by means of the user through an interactive screen shown in the computer screen D, by means of any peripheral input device (mouse, touch screen, keyboard, etc.).

FIGS. 2 to 11 show different screenshots corresponding to different screens of the dynamic webpage GUI generated and provided by the method of the present invention, for three different embodiments, which are next explained and named as Example 1, Example 2 and Example 3.

Figure 2:
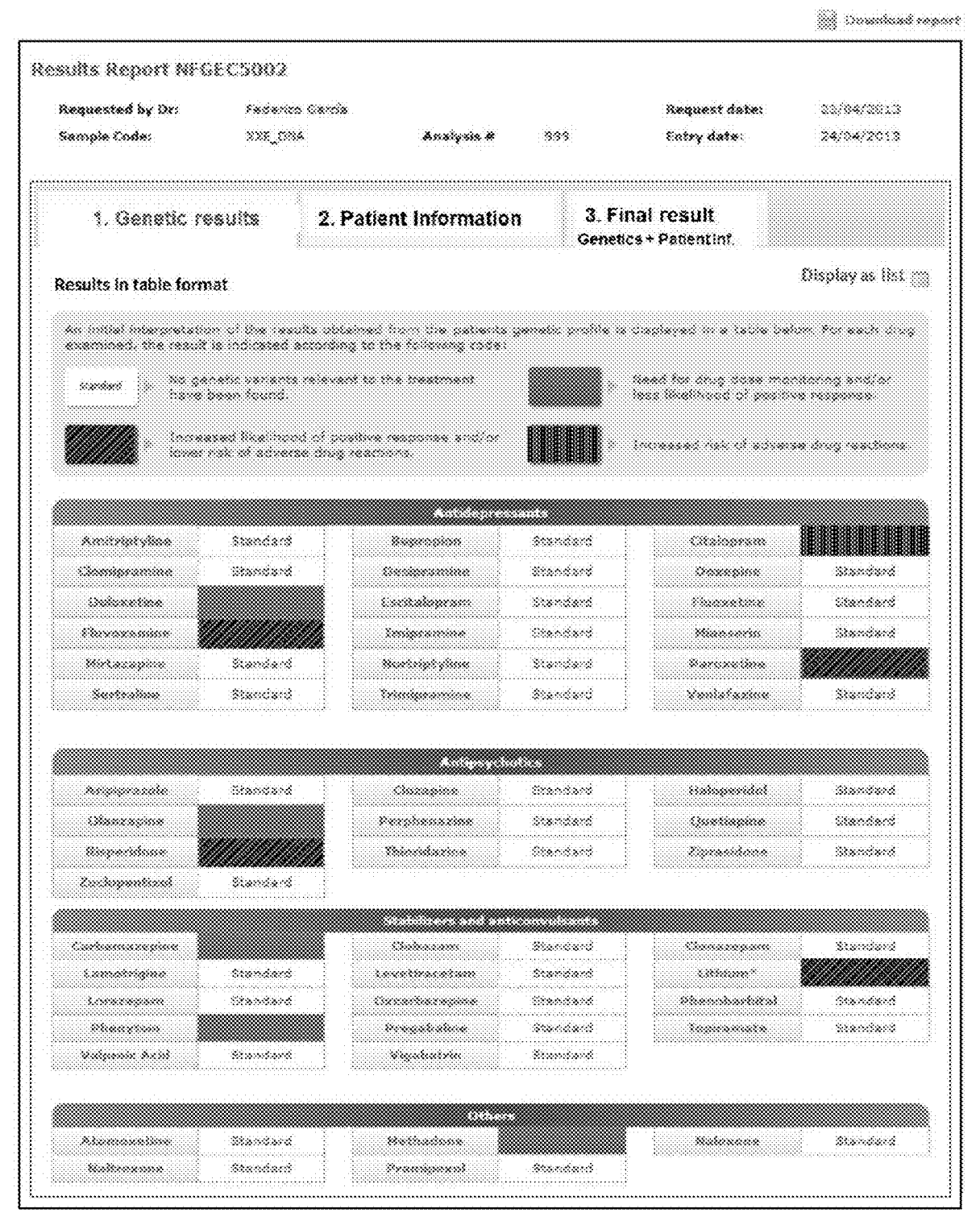
Figure 3:
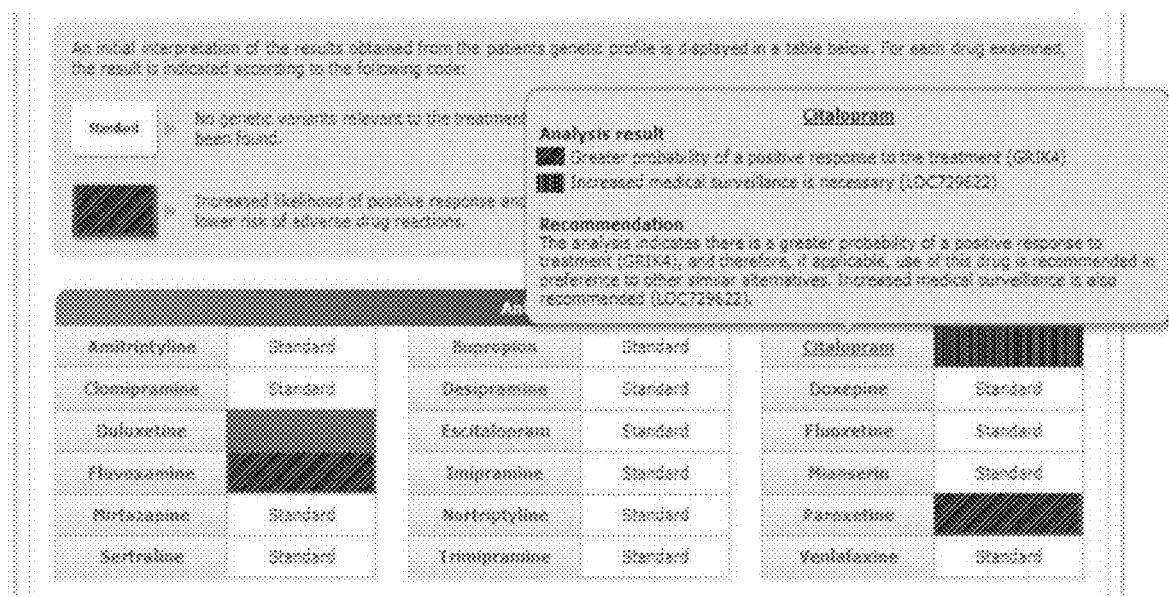
FIG. 3 shows part of the first screen shown in FIG. 2, also for Example 1, but once a balloon with additional recommendation information has appeared upon the user positioning the mouse pointer over the name of the underlined drug, i.e. on Citalopram.
Figure 4:
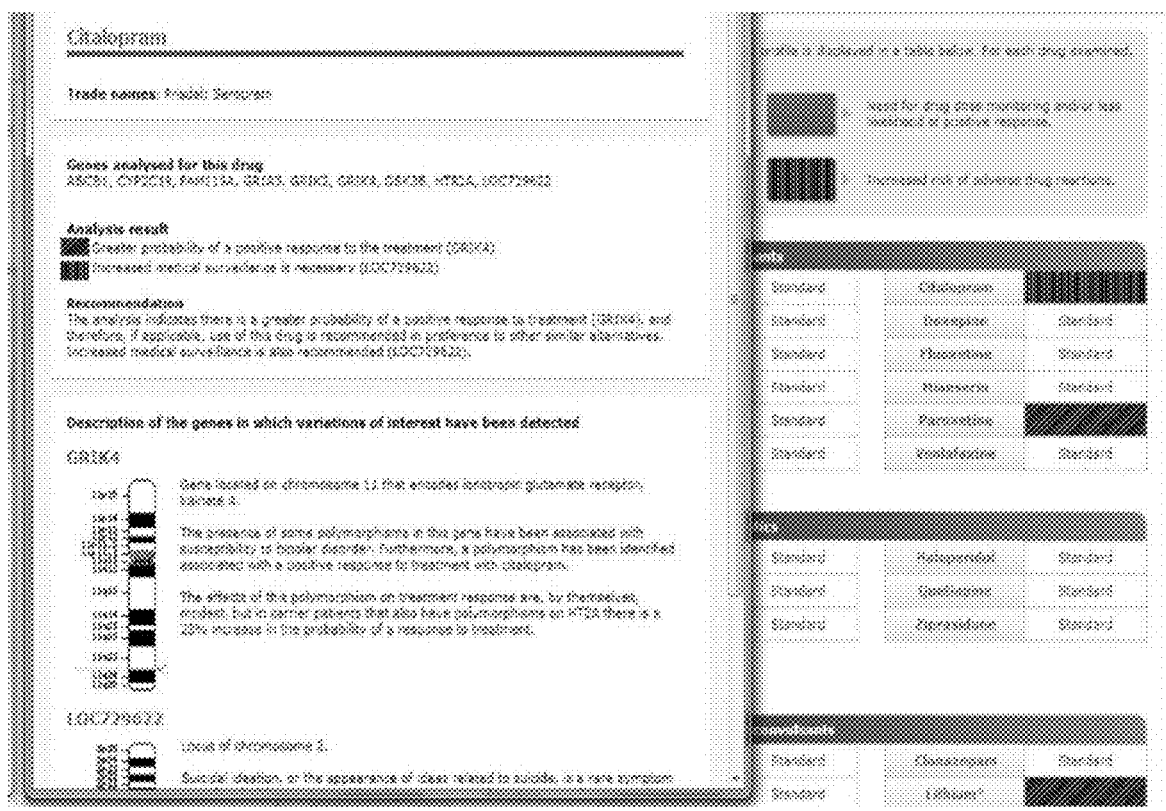
FIG. 4 also relates to Example 1 of the method of the present invention, and shows part of the first screen shown in FIG. 2, but once a pop-up window with further additional information, including genes and variants of interest, has appeared upon the user has clicked on the name of the drug underlined in FIG. 3, i.e. on Citalopram.

Example 1 (FIGS. 2 to 4)

In FIG. 2, a first screen of the dynamic webpage GUI, corresponding to the tab labeled as "Genetic results", is displayed. Said first screen includes four charts, each including a plurality of identifiers of respective drugs (particularly the name thereof) having the same or a similar purpose, in particular said four charts include charts for drugs which act as antidepressants, antipsychotics, stabilizers and anticonvulsants and others.

Each drug identifier is shown associated to one of the displayed personalized recommendations generated for a particular patient. There are four main kinds of personalized recommendations displayed in FIG. 1, displayed as follows:

- those depicted by means of a white rectangle (and with the legend "Standard" written therein) correspond to personalized recommendations having associated thereto a standard drug response, standard metabolism and/or standard risk of adverse drug reactions, i.e. were in the patient genetic data no genetic variants relevant to the treatment with the corresponding drug have been found.
- those depicted with a grey rectangle with oblique black lines therein (alternatively and preferably, this rectangle should be a green and plain rectangle) correspond to personalized recommendations having associated thereto an increased likelihood of positive response and/or lower risk of adverse drug reactions.
- those depicted with a grey plain rectangle (alternatively and preferably, this rectangle should be an amber and plain rectangle) correspond to personalized recommendations having associated thereto a lower probability of drug positive response and/or the need for a specific dosage monitoring, i.e. an increased likelihood of positive response and/or lower risk of adverse drug reactions.
- those depicted with a grey rectangle with vertical lines therein (alternatively and preferably, this rectangle should be a red and plain rectangle); this personalized recommendations are the most highlighted ones (as mentioned, preferably in red) according to a risk criterion, as they correspond to personalized recommendations having associated thereto an increased risk of adverse drug reactions.

As shown in FIG. 2, this case highlights the pharmacogenetic analysis for the antidepressant drug Citalopram, i.e. this is the drug associated to the most highlighted personal recommendation (to make the user pay more attention to it), due to its risk, according to the acquired and analyzed patient genetic information, of adverse drug reactions for said patient.

Once the user positions the mouse pointer over the name of the underlined drug, i.e. on Citalopram, as shown in FIG. 3, a balloon with additional recommendation information appears. This additional recommendation information shows the analysis results for Citalopram including the identified genetic variant also classified according to a risk criterion, in this case with the same graphical code used for the personalized recommendations of the drugs used in FIG. 2 (although a color code is also preferred, including the red color for highlighting the highest risk identified genetic variant) together with respective description pieces in the form of phrases.

As shown in said balloon, in this particular example, two different genetic variants were identified, one (GRIK4) associated with a higher probability of a positive response to Citalopram (displayed with a grey rectangle with oblique black lines therein, although it should be preferably displayed in green) and a second variant (LOC729622) associated with an increased risk of adverse drug reactions (displayed with a grey rectangle with vertical black lines therein, although it should be preferably displayed in red), requiring an increased medical surveillance.

Integration of these two pieces of information is displayed in the first screen drugs chart, i.e. in that shown in FIG. 2, as a single personalized recommendation with a grey rectangle with vertical black lines therein (although it should be preferably displayed in red), according to a defined risk criterion, associated in this case to Citalopram. In other words, the graphical code (grey rectangle with vertical black lines) displayed in the balloon for the recommendation information of the genetic variant associated to an increase risk of adverse effect (LOC729622) is the same displayed in FIG. 2 for representing the single personalized recommendation for Citalopram.

If the user clicks on the name of Citalopram then, as shown in FIG. 4, a pop-up window appears, which includes, apart from the information already shown in the balloon of FIG. 3, further additional information regarding the genes and variants of interest analyzed for the drug, in the form of the above mentioned description pieces or phrases describing how the presence/absence of a specific genetic variant affects the drug response and/or adverse drug reactions.

At the upper right corner of the first screen shown in FIG. 2 there is a virtual icon with the legend "Download report". When the user clicks on this virtual icon he downloads the above mentioned PDF file generated at block 8 of FIG. 1.

There is also another virtual icon shown in FIG. 2, in this case with the legend "Display as list" placed adjacent thereto. When the user clicks on this virtual icon the information included in the charts of FIG. 2 is alternatively displayed in the form of a list.

Example 2 (FIGS. 5 to 8)

This case highlights selection of a treatment of choice plus selection of a concomitant medication and how the influence of said concomitant medication modifies the displayed drug chart and the final personalized recommendation. The pharmacogenetic analysis results report is the same as in Example 1 (i.e. the one shown in FIG. 2).

Figure 5:
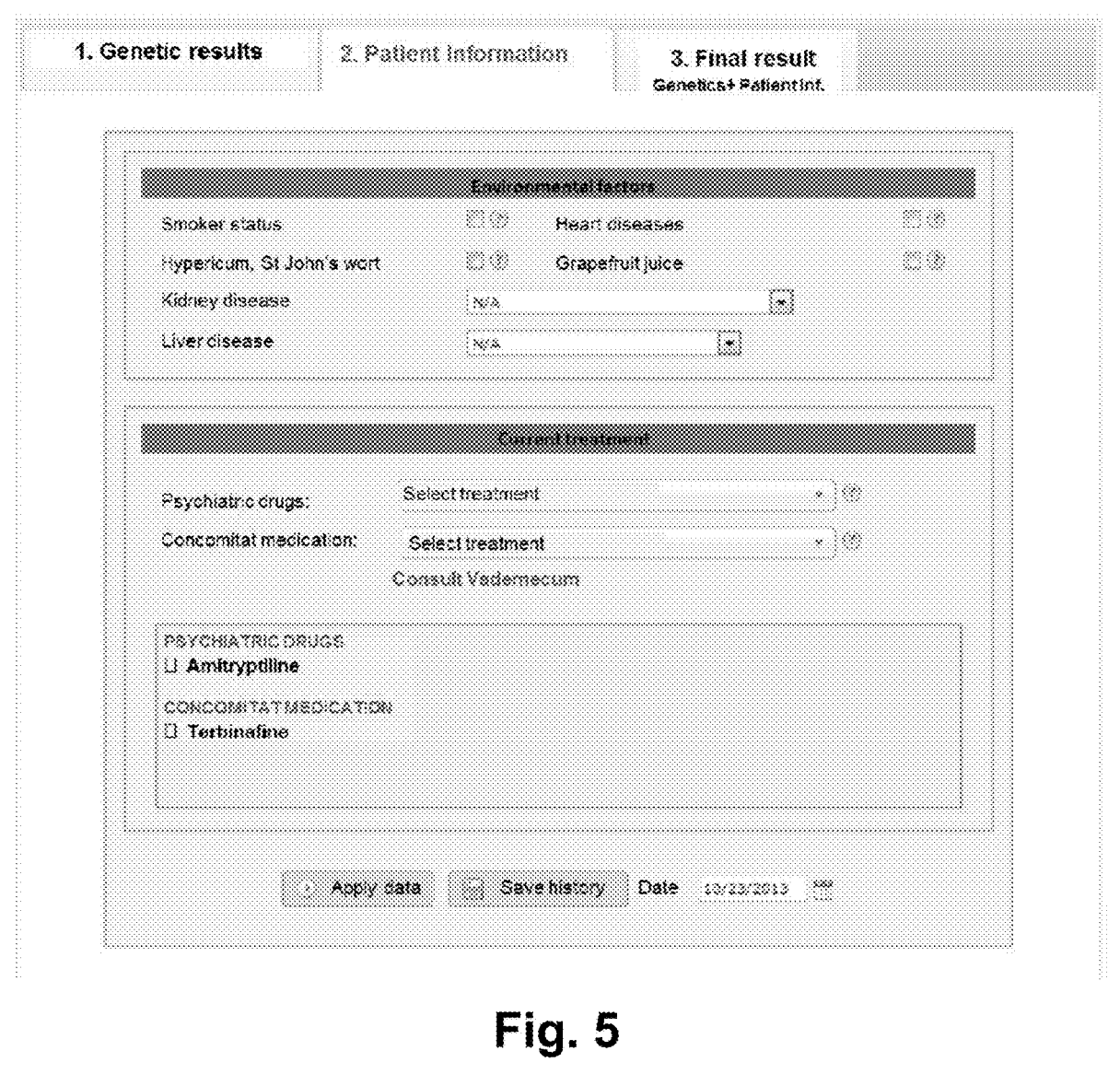

In FIG. 5, a second screen of the dynamic webpage GUI corresponding to the tab labeled as "Patient Information" is displayed. Said second screen includes a plurality of fillable boxes to be filled by a user to input information regarding the patient, including concomitant medication or substances and personal information associated to pathologies and/or habits affecting health and/or to physical characteristics, including at least one of anthropometric data, ethnicity, age and gender.

Said personal information is grouped under the heading "Environmental factors", and for the illustrated embodiment includes the next first kind of fields: "Smoker Status", "Hypericum, St John's wort", "Heart diseases" and "Grapefruit juice", all of them, adjacent to a box which the user only has to mark if the patient meets them, and also the next second kind of fields: "Kidney disease" and "Liver disease" adjacent to a box which when clicked by the user shows a drop-down list with several selectable options.

Under the heading "Current treatment", there are two fields: a first one referred as "Psychiatric drugs" adjacent to a box which when clicked by the user shows a drop-down list including the drugs shown in FIG. 2 in order to select the psychiatric drug or drugs of choice, and a second field referred as "Concomitant medication" adjacent to a box which when clicked by the user shows a drop-down list including several selectable non-psychiatric drugs.

Below said fields, there is a rectangular area into which the psychiatric drug and concomitant medication selected for the illustrated embodiment are shown, in this case the physician has selected Amitryptiline as treatment of choice, which according to the results of the pharmacogenetic analysis is indicated as "Standard" for this patient (see FIG. 2), and Terbinafine as concomitant medication.

Once the psychiatric drug and concomitant medication have been selected, the user clicks on the "Apply data" button placed below in order the selections be applied, and, optionally, to the "Save history" button to add to a history file the selected options.

This information is processed together with the pharmacogenetic data and the resulting combined information and specific recommendations are displayed in the third screen (tab "Final result") of the dynamic webpage GUI, as shown in FIG. 6.

FIG. 6 shows the same charts and drugs shown in FIG. 2 but with the personalized recommendations modified based on the information inputted in the second screen. Among others, particularly the personalized recommendation for the drug Haloperidol has changed from displaying a white rectangle (see FIG. 2) to a grey rectangle with vertical lines (see FIG. 6), and the drug Amitriptyline from a white rectangle to a grey plain rectangle.

Some circled exclamation mark icons have also been added to some of the personalized recommendations, meaning that the drugs to which they refer have some reported interactions which can be consulted if placing the mouse pointer on the drug name, in the form of a balloon, or if clicking thereon, in the form of a pop-up window. The possible reported interactions are shown in FIG. 6 together with respective virtual icons representing the following categories: "Contraindication", "Not recommended combination", "Warning/Information", "Modify regimen and/or monitor parameters", "Increase dose and/or monitor parameters" and "Reduce dose and/or monitor parameters".

Figure 7A:
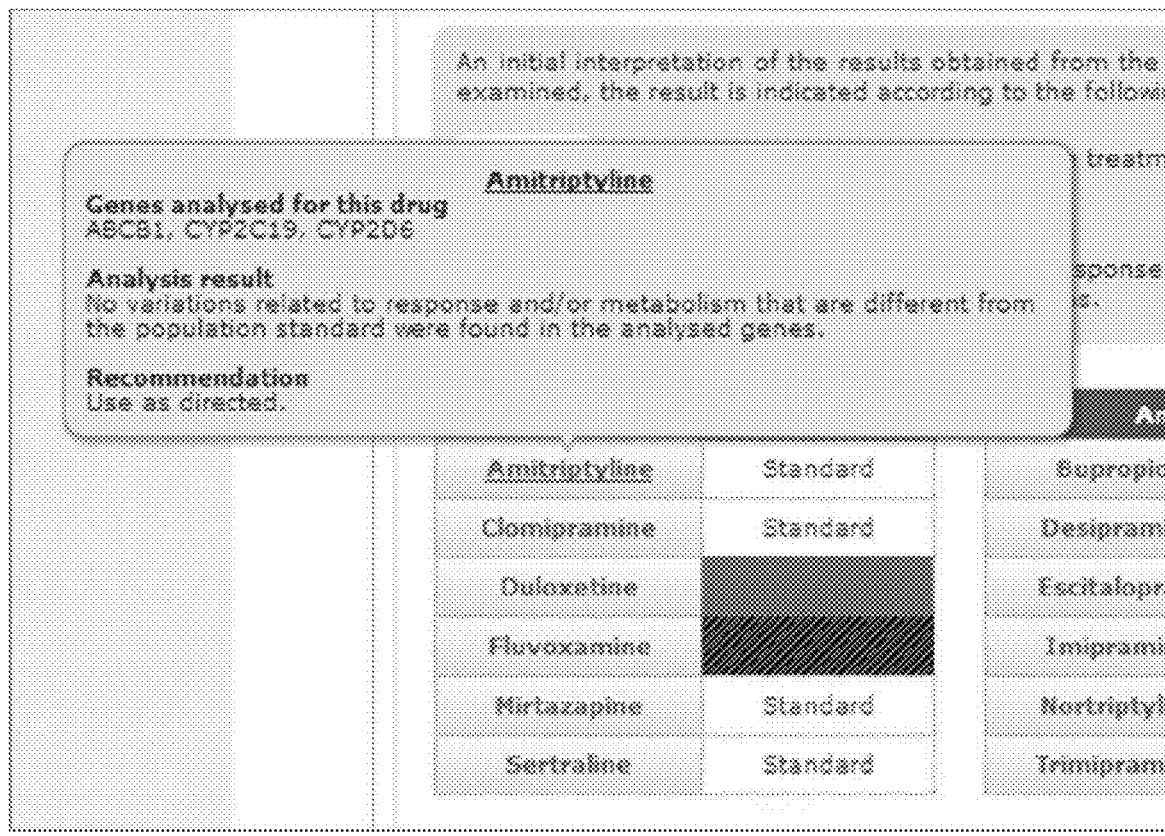
FIG. 7a shows part of the first screen shown in FIG. 2, i.e. with the recommendations not yet modified based on the information inputted in the second screen, including a balloon with additional recommendation information which has appeared upon the user positioning the mouse pointer over the name of the underlined drug, i.e. on Amitriptyline.
Figure 7B:
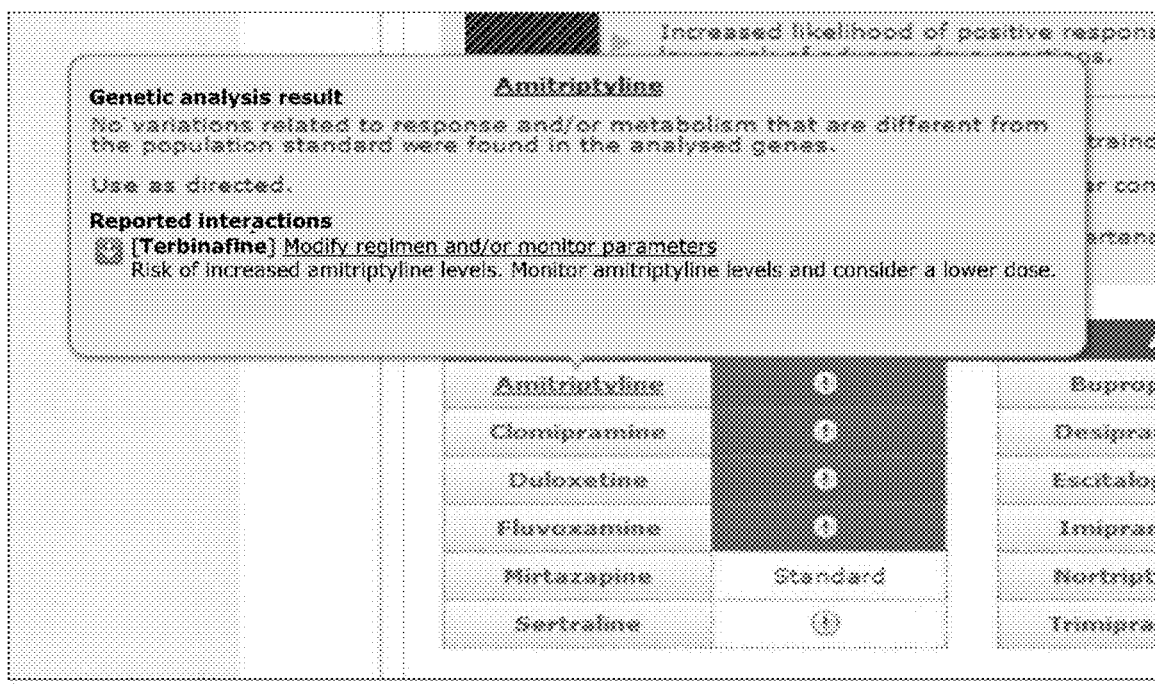
FIG. 7b shows, also for Example 2, part of the first screen shown in FIG. 6, i.e. with the recommendations already modified based on the information inputted in the second screen, including a balloon with additional recommendation information which has appeared upon the user positioning the mouse pointer over the name of the underlined drug, i.e. on Amitriptyline, said additional recommendation information being different to the one shown in FIG. 7a as a result of the influence of the inputted information.

By comparing FIG. 7a, corresponding to Example 1, with FIG. 7b, which corresponds to Example 2, it can be seen that the information given in the balloons associated to Amitriptyline has changed, reporting the balloon of FIG. 7b that the concomitant medication Terbinafine acts as a potent inhibitor of the metabolism of Amitriptyline by the CYP2D6 enzyme in the liver.

This drug-concomitant medication interaction is depicted with a grey plain rectangle (although, preferably it should be highlighted in amber) in the third screen of the dynamic webpage, as shown in FIGS. 6 and 7b.

Accordingly the specific personalized recommendation for Amitriptyline has changed from "Use as directed" to "Risk of an increase in Amitriptyline plasmatic levels. Monitor Amitriptyline plasmatic levels and reduce the dose if required", which is classified in the "Modify regimen and/or monitor parameters" category.

Figure 8A:
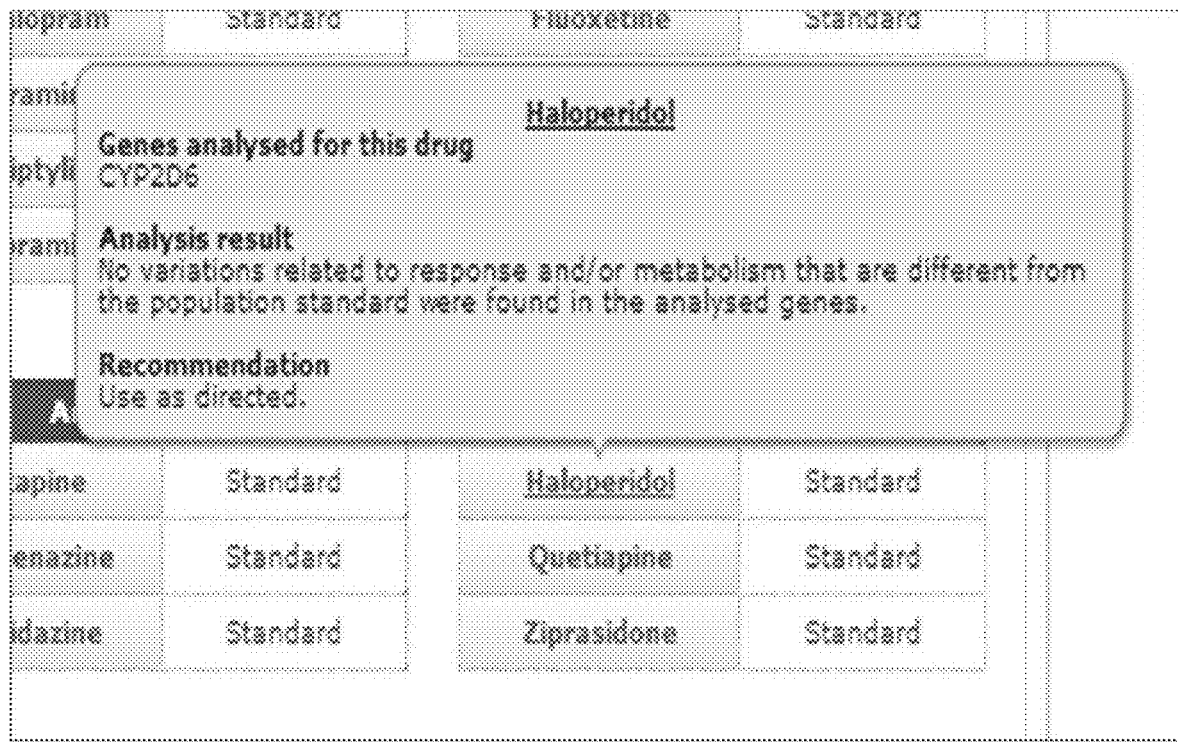
FIGS. 8a and 8b are equivalent, respectively, to FIGS. 7a and 7b but for a different drug, particularly for Haloperidol; the additional recommendation information for said drug displayed in the balloon of FIG. 8b has also been modified with respect to the one shown in the balloon of FIG. 8a, as a result of influence of the information inputted in the second screen.
Figure 8B:
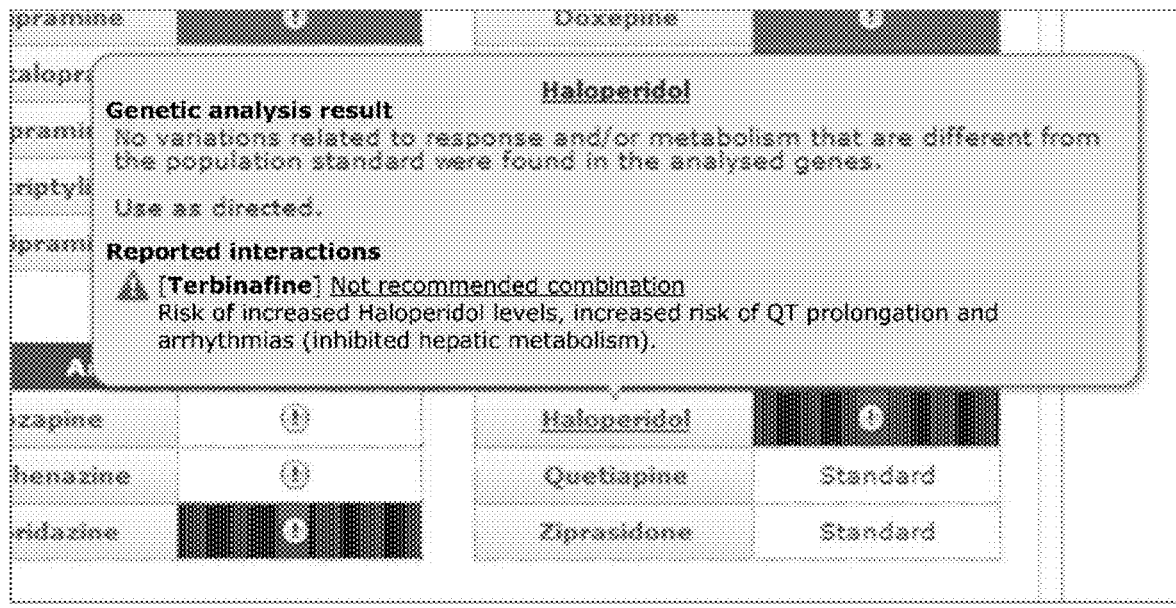

Terbinafine also acts as a potent inhibitor of the hepatic metabolism of Haloperidol. In this case, as stated above selecting Terbinafine as concomitant medication has changed the results of the pharmacogenetic analysis for Haloperidol (initially indicated as "Standard") to a personalized recommendation of a risk of an increase in Haloperidol plasmatic levels and therefore a higher risk of prolongation of the QT interval and arrhythmias, as shown in the balloon of FIG. 8b.

Figure 9:
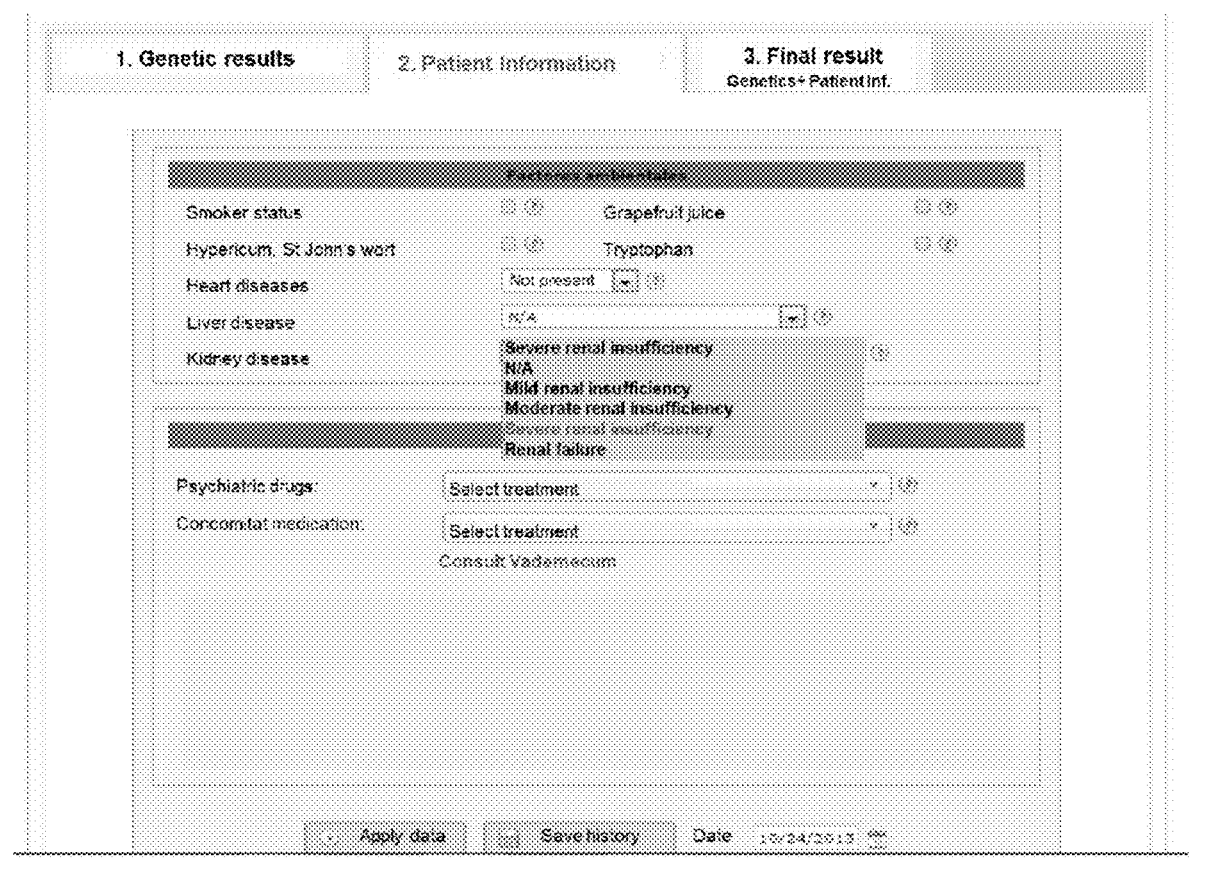
Figure 10:
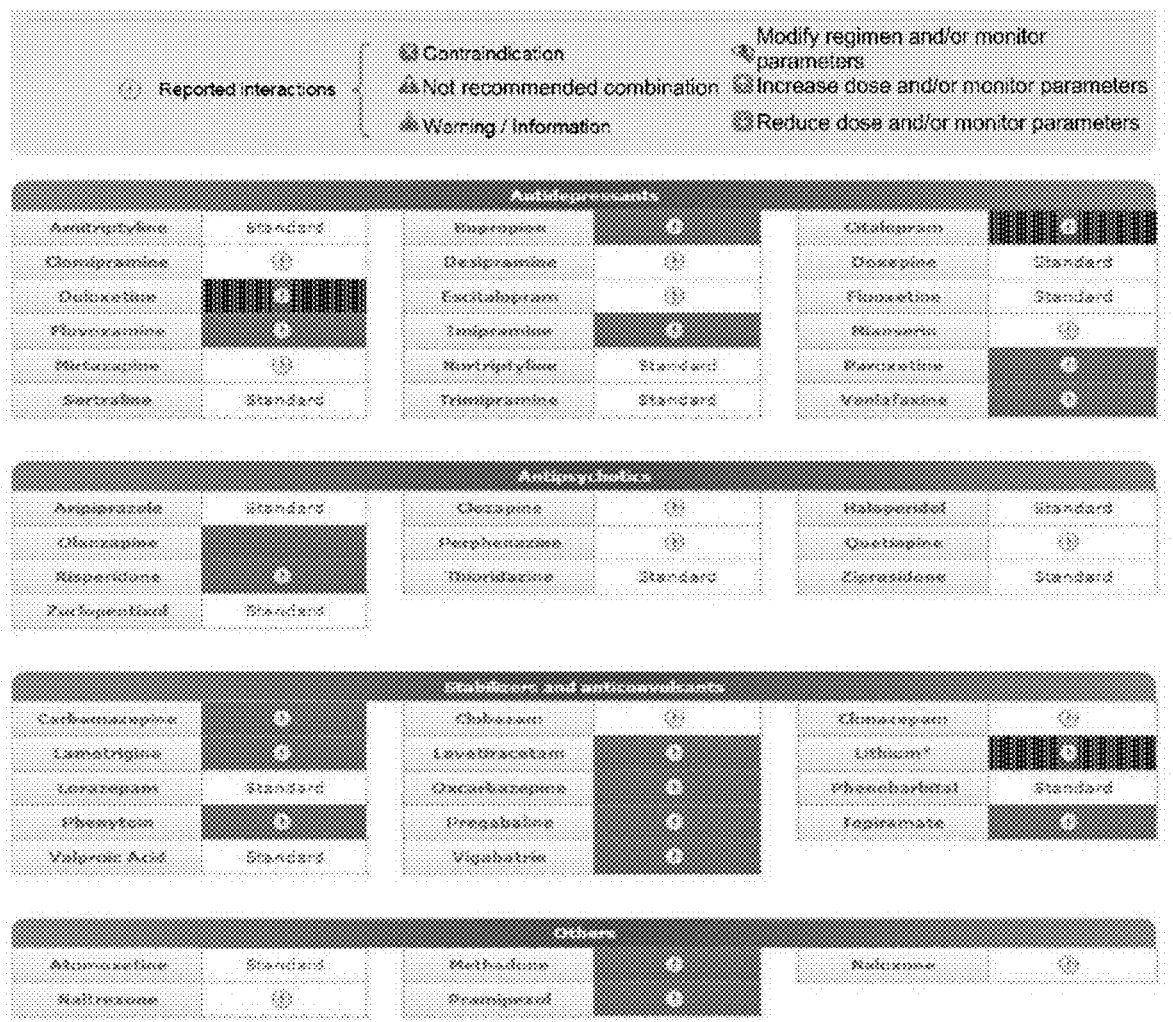
FIG. 10 shows, for Example 3, a screen shot of a third screen of the dynamic webpage GUI of the method of the present invention, which corresponds to the first screen shown in FIG. 2 but once the displayed recommendation information has been modified as a response to the information inputted by the user in the second screen according to FIG. 9.
Figure 11A:
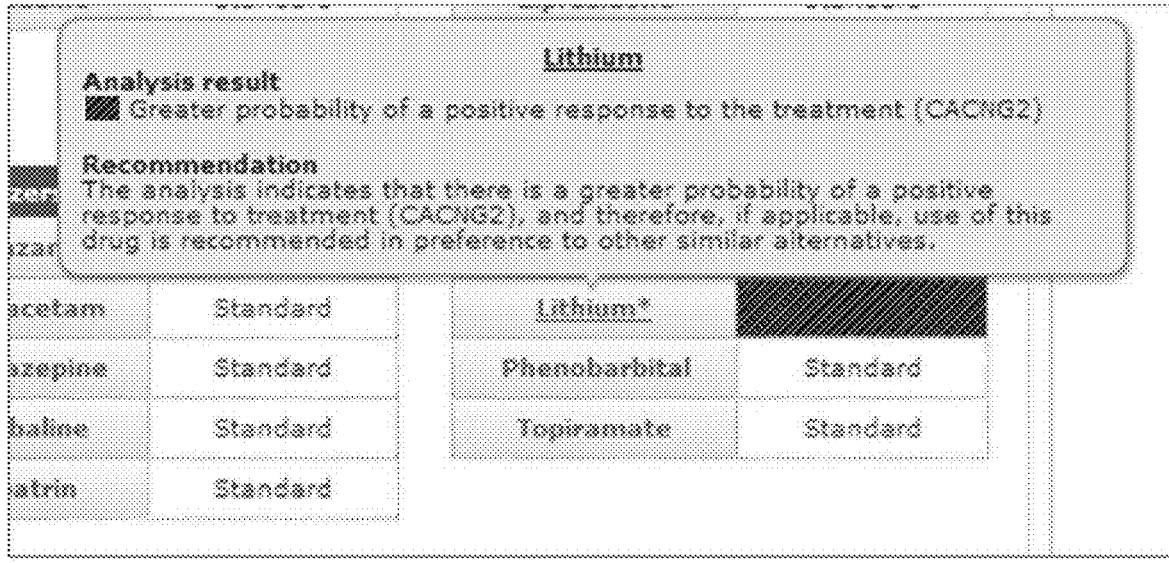
FIGS. 11a and 11b are similar to FIGS. 7a and 7b, but for Example 3 and for Lithium; where the additional recommendation information for said drug displayed in the balloon of FIG. 11b has also been modified with respect to the one shown in the balloon of FIG. 11a, as a result of influence of the information inputted in the second screen according to FIG. 9.

Example 3 (FIGS. 9 to 11)

This case highlights selection of a comorbid pathology present in the patient and how the influence of said comorbid pathology modifies the displayed drug chart and the final personalized recommendation. The pharmacogenetic analysis results report is also the same as in Example 1 (i.e. the one shown in FIG. 2).

In this example in the second screen (tab) of the dynamic webpage the physician selected "Severe renal insufficiency" in the "Kidney disease" field, as shown in FIG. 9.

Figure 11B:
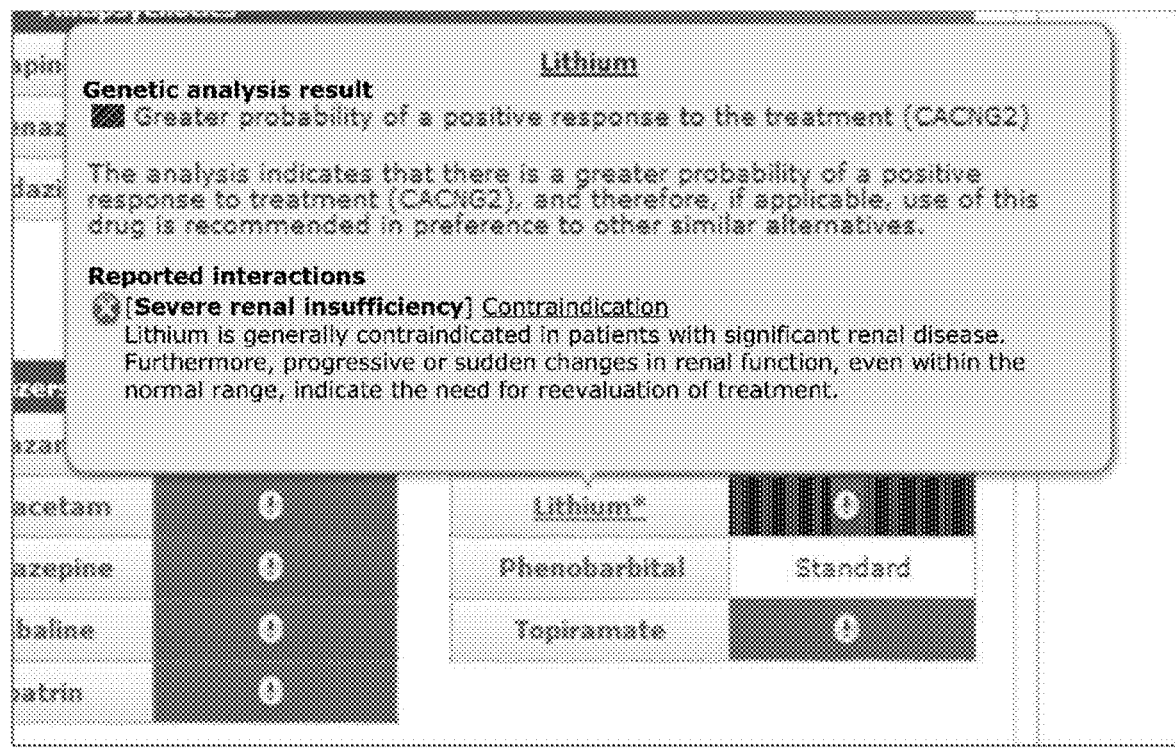

As shown in FIG. 10, which shows the third screen of the dynamic webpage, this action has changed the charts and personalized recommendations initially displayed in FIG. 2. For instance, Lithium has appeared in FIG. 2 associated to a grey rectangle with oblique black lines therein (although it should be preferably displayed in green) and the display has changed to a grey rectangle with vertical lines therein in FIG. 10 (alternatively and preferably, this rectangle should be a red rectangle), highlighting the fact that Lithium is contraindicated in patients with severe kidney impairment. The detailed information of this warning is shown in a balloon when the physician positions the mouse pointer over the name of the drug (as shown in FIG. 11b) or is shown in a pop-up window when the name of the drug is clicked.

A person skilled in the art could introduce changes and modifications in the embodiments described without departing from the scope of the invention as it is defined in the attached claims.

The invention claimed is:

1. A web-based computer-aided method for providing personalized recommendations about drug use, comprising performing the following steps:

acquiring, by a processor, genetic information about a patient, including single nucleotide polymorphisms (SNPs), said genetic information including information regarding genes and genetic variants associated to metabolism and information regarding genes and genetic variants which are not associated to metabolism, said information regarding genes and genetic variants which are not associated to metabolism being related to genes and genetic variants associated to drug response and adverse drug reactions;

processing, by a processor, said acquired genetic information together with selected pharmacogenetic information about several drugs to generate personalized pharmacogenetic information for said patient, the selected pharmacogenetic information including descriptive information pieces correlating each drug of said several drugs with the presence/absence of a specific genetic variant, each of said descriptive information pieces having associated thereto a risk degree;

automatically generating and displaying, by a web server, in a first screen or first graphical area of a user display, a results report that includes a plurality of personalized recommendations for said patient, regarding a drug response, drug metabolism and/or adverse drug reactions to the several drugs, from said generated personalized pharmacogenetic information;

visually highlighting, by the web server, among said plurality of displayed personalized recommendations, those recommendations associated to risk of adverse drug reactions, following a risk criterion; and generating, by the web server, a dynamic webpage from contents regarding at least said plurality of personalized recommendations, providing a graphical user interface (GUI) from said dynamic webpage, said displaying and visually highlighting of personalized recommendations being performed using said graphical user interface (GUI);

wherein the method further comprises:

acquiring, by a processor, information about at least one concomitant medication or substance being taken by said patient, and inputting the acquired information in a second screen or second graphical area;

checking if the concomitant medication or substance modifies the results report by consulting a database that comprises data about an influence of the concomitant medication or substance on the drug response, on drug levels comprising absorption, distribution, metabolism, and excretion, and/or adverse drug reactions or based on an influence of said drug on a concomitant medication/substance response, on a medication/substance metabolism, and/or on adverse medication/substance reactions; and generating and displaying a new dynamic report in a third screen or third graphical area if the concomitant medication or substance has modified the results report.

2. The method of claim 1, comprising:

when there is only one of said descriptive information pieces correlating a drug with a respective genetic variant of said genetic information, retrieving said only one descriptive information piece and generating therefrom a personalized recommendation for said patient, regarding said drug, and when there are at least two of said descriptive information pieces correlating a drug with at least two respective genetic variants of said genetic information, retrieving said at least two descriptive information pieces and generating a personalized recommendation for said patient, regarding said drug, by selecting, out of said at least two retrieved description information pieces, the descriptive information piece with the highest risk degree.

3. The method of claim 1, wherein said drugs are neuropsychiatric drugs.

4. The method of claim 1, comprising performing said interaction analysis after said generation of personalized pharmacogenetic recommendations, wherein said modifying of at least part of said personalized recommendations is performed on the already generated personalized recommendations.

5. The method of claim 4, wherein for a case where said at least one concomitant medication or substance is in a number of at least two, the method comprises, based on the influence of each concomitant medication/substance on said drug or vice versa, generating at least two provisional modified personalized recommendations, each having associated thereto a risk degree, and generating and displaying a final modified personalized recommendation for said patient, regarding said drug, by selecting, out of said at least two provisional modified personalized recommendations, the provisional personalized recommendation with the highest risk degree.

6. The method of claim 1, comprising performing said interaction analysis as part of said processing of acquired genetic information and selected pharmacogenetic information, said processing thus including the processing of said acquired information about at least one concomitant medication or substance together with said acquired genetic information and said selected pharmacogenetic information, wherein said modifying of at least part of said personalized recommendations takes place during, and forms part of, the generation of personalized recommendations.

7. The method of claim 1, further comprising acquiring information about further personal information of said patient associated to pathologies and/or to habits affecting health and/or to physical characteristics including at least one of anthropometric data, ethnicity, age and gender, and inputting the acquired information in the second screen or second graphical area, and generating and displaying the new dynamic report based also on the influence of said further personal information.

8. The method of claim 1, wherein said personalized recommendations are displayed according to a color code, said visual highlighting including at least the use of a conspicuous or eye-catching or flashing color for the personalized recommendation to be highlighted according to said risk criterion.

9. The method of claim 8, wherein said color code is used for displaying:
   in red, a personalized recommendation having associated thereto an increased risk of adverse drug reactions;
   in amber, a personalized recommendation having associated thereto a lower probability of drug response and/or the need for a specific dosage monitoring;
   in green, a personalized recommendation having associated thereto a higher probability of drug response and/or a lower risk of adverse drug reactions; and
   in white, a personalized recommendation having associated thereto a standard drug response, standard metabolism and/or standard risk of adverse drug reactions.

10. The method of claim 7, further comprising changing a color and/or shape of the third screen or third graphical area based on the information inputted in the second screen or second graphical area.

11. The method of claim 1, comprising displaying a plurality of charts, each including a plurality of identifiers of respective drugs having the same or a similar purpose, wherein each drug identifier is shown associated to one of said displayed personalized recommendations.

12. The method of claim 10, wherein:
   the first screen or first graphical area includes a plurality of charts, each including a plurality of identifiers of respective drugs having the same or a similar purpose, wherein each drug identifier is shown associated to one of the user displayed personalized recommendations;
   the second screen or second graphical area includes a plurality of fillable boxes to be filled by a user to input information regarding the patient, including the concomitant medication or substances and the personal information; and
   the third screen or third graphical area includes said plurality of charts having modified at least part of said personalized recommendations and the way they are displayed, based on the influence of the concomitant medication or substances and of said personal information.

13. The method of claim 1, further comprising performing a learning feedback process from statistical information regarding several drugs responses and/or several patients and/or interactions between drugs and concomitant medication or substances and/or interactions between drugs and patients personal information associated to pathologies and/or habits affecting health, and/or to physical characteristics including at least one of anthropometric data, ethnicity, age and gender, wherein the generation of said personalized recommendations is also based on the outcomes of said learning feedback process.

14. A non-transitory computer-readable medium containing program instructions for a computer to perform a web-based method for providing personalized recommendations about drug use, comprising performing the following steps:
   acquiring genetic information about a patient, including single nucleotide polymorphisms (SNPs), said genetic information including information regarding genes and genetic variants associated to metabolism and information regarding genes and genetic variants which are not associated to metabolism, said information regarding genes and genetic variants which are not associated to metabolism being related to genes and genetic variants associated to drug response and adverse drug reactions;
   processing said acquired genetic information together with selected pharmacogenetic information about several drugs to generate personalized pharmacogenetic information for said patient, the selected pharmacogenetic information including descriptive information pieces correlating each drug of said several drugs with the presence/absence of a specific genetic variant, each of said descriptive information pieces having associated thereto a risk degree;
   generating and displaying in a first screen or first graphical area of a user display a results report that includes a plurality of personalized recommendations for said patient, regarding a drug response, drug metabolism and/or adverse drug reactions to the several drugs, from said generated personalized pharmacogenetic information;
   visually highlighting, among said plurality of displayed personalized recommendations, those recommendations associated to risk of adverse drug reactions, following a risk criterion; and
   generating a dynamic webpage from contents regarding at least said plurality of personalized recommendations, providing a graphical user interface (GUI) from said dynamic webpage, said displaying and visually highlighting of personalized recommendations being performed using said graphical user interface (GUI);
   and
   wherein the program instructions further comprises:
   acquiring information about at least one concomitant medication or substance being taken by said patient, and inputting the acquired information in a second screen or second graphical area;
   checking how the concomitant medication or substance modifies the results report by consulting a database that comprises data concerning an influence of the concomitant medication or substance on the drug response, on drug levels comprising absorption, distribution, metabolism, and excretion, and/or adverse drug reactions or based on an influence of said drug on a concomitant medication/substance response, on a medication/substance metabolism, and/or on adverse medication/substance reactions; and generating and displaying a new dynamic report in a third screen or third graphical area if the concomitant medication or substance has modified the results report.

\* \* \* \* \*